United States Patent [19]
Fisher et al.

[11] Patent Number: 5,644,051
[45] Date of Patent: Jul. 1, 1997

[54] INTERMEDIATES FOR THE PREPARATION OF CARBACEPHEMS

[75] Inventors: Jack W. Fisher; Lowell D. Hatfield; Richard C. Hoying; James E. Ray, all of Indianapolis, Ind.

[73] Assignee: Eli Lilly and Company, Indianapolis, Ind.

[21] Appl. No.: 444,118

[22] Filed: May 18, 1995

Related U.S. Application Data

[62] Division of Ser. No. 837,173, Feb. 18, 1992, Pat. No. 5,521,307.

[51] Int. Cl.$^6$ .................... C07D 471/04; C07D 413/04; C07B 43/04
[52] U.S. Cl. .................................................. 540/205
[58] Field of Search ............................... 540/205

[56] References Cited

U.S. PATENT DOCUMENTS

| | | | |
|---|---|---|---|
| 4,665,171 | 5/1987 | Evans et al. | 540/365 |
| 5,095,107 | 3/1992 | Blanchard | 540/205 |

FOREIGN PATENT DOCUMENTS

| | | |
|---|---|---|
| 0 362 902 | 4/1990 | European Pat. Off. . |
| 0 365 190 | 4/1991 | European Pat. Off. . |

OTHER PUBLICATIONS

Jackson et al., Synthesis of Carbacephem Antibiotics:Synthesis via Dieckmann Reaction Using Phenylesters to Direct the Regioselectivity of the Cyclization, 31 Tetrahedron Letters 6317 (1990).
Muller et al., Helvetica Chimica Acta, vol. 74:767–773 (1991).

(List continued on next page.)

*Primary Examiner*—Mark L. Berch
*Attorney, Agent, or Firm*—Kathleen R. S. Page; Thomas G. Plant

[57] ABSTRACT

This invention is directed to carbacephems and methods for their preparation:

In the foregoing formulae, $R^3$ represents phenyl, $C_1$–$C_4$ alkylphenyl, halophenyl, $C_1$–$C_4$ alkoxyphenyl, naphthyl, thienyl, furyl, benzothienyl, or benzofuryl.

10 Claims, No Drawings

OTHER PUBLICATIONS

Spitzer, J. Org. Chem. 39:2468 (1974).
Liotta, J. Org. Chem. 45:2887 (1980).
Piatak, J. Org. Chem. 34:116 (1969).
Ayers et al., J.C.S. Chem. Comm., 1972, p. 428.
Wolfe et al., Chem. Comm., 1970, pp. 1420–1421.
Caputo et al., The Oxidation of Cyclobutanols and Aromatic Rings with Ruthenium Tetroxide, 47 Tetrahedron Letters 4729–4731 (1967).
Klein et al., Umsetzung Adsorbierter Aromaten Mit Ozon, 48 Tetrahedron Letters 4249–4250 (1975).
Deno et al., Aromatic Ring Oxidation of Alkylbenzenes, 20 Tetrahedron Letters 1703–1704 (1977).

INTERMEDIATES FOR THE PREPARATION OF CARBACEPHEMS

This application is a division of application Ser. No. 07/837,173 filed Feb. 18, 1992, now U.S. Pat. No. 5,521,307.

BACKGROUND OF THE INVENTION

1. Field of the Invention

The present invention relates to the preparation of 1-carbacephems, such as the 1-carba(1-dethia)-3-cephem-4-carboxylic acids, and relates particularly to compounds and methods useful in such preparation. The invention provides novel methods which are readily performed and give high yield of product. Also provided are novel compounds which are useful for a variety of purposes, including as intermediates in the inventive processes.

2. Description of the Prior Art

The 1-carba(1-dethia)-3-cephem-4-carboxylic acids, hereafter the 1-carbacephalosporins or cephalosporin analogs, are known to be useful as antibiotics. Because of the importance of these newer β-lactam antibiotics, there is a need for improved methods for their preparation.

The preparation of 1-carbacephalosporins and C-3 substituted methyl derivatives thereof is taught broadly by Christensen et al. in U.S. Pat. No. 4,226,866. Hirata et al., in U.K. Patent Application No. 2041923, teach a process for preparing 3-H and 3-halo 1-carbacephalosporins, while Hatanaka et al., Tetrahedron Letters, 24, No. 44, pp. 4837–4838 (1983), teach a process for preparing a 3-hydroxy-(±)-1-carbacephalosporin.

In U.S. Pat. No. 4,665,171, issued to Evans et al. on May 12, 1987, there is described the [2+2] cycloaddition reaction of a chiral auxiliary and an imine to produce the chiral azetidinone. Specifically, a 4(S)-aryloxazolidin-2-one-3-ylacetyl halide, i.e. the chiral auxiliary, is reacted with an imine derived from a benzylamine and a 3-arylacrolein (e.g., cinnamaldehyde) to yield a 3β-[4(S)-aryloxazolidin-2-one-3-yl]azetidin-2-one intermediate. The intermediates are characterized by a four member nitrogen ring having coupled thereto an N-benzyl group, the chiral auxiliary, and a —C2—R' group (where R' is phenyl, furyl or naphthyl).

As described by Evans, the intermediate compounds are converted to 1-carbacephalosporins through a multistep process. However, in order to be useful for the synthesis of carbacephems, the intermediates must first be modified by the removal of the chiral auxiliary and the N-benzyl group by a classical birch reduction. The resulting compound is reacylated with phenoxyacetyl chloride and elaborated to the diazo ketone, and then to the key enol intermediate. The enol is in turn converted to the loracarbef nucleus by standard enol chlorination and side-chain cleavage.

The Evans procedure is a useful synthesis route, but has several disadvantages. The exchange of the protective groups is especially undesirable. The chiral auxiliary is replaced by a V-side chain, and the N-benzyl group is reduced to the N-H function necessary for the key diazo insertion reaction. The only known method for removing the chiral auxiliary is a birch reduction, which method is incompatible with the 3-chlorocephem nucleus. Also, the diazo insertion chemistry is dependent on the use of a rhodium catalyst, which is undesirable because of cost and negative environmental impact.

Synthesis of carbacephems using a modified Dieckmann cyclization is described in B. G. Jackson et al., "Synthesis of Carbacephem Antibiotics: Synthesis Via Dieckmann Reaction Using Phenyl Esters to Direct the Regioselectivity of the Cyclization," Tetrahedron Letters, Vol. 31, No. 44, pp. 6317–6320 (1990). However, the Dieckman process depended on the resolution of a mixture of key amino acids by the selective enzymatic acylation of only the desired amino acid isomer. The resulting acylated product is converted to a key precursor, which upon base cyclization gives the enol.

This achiral Dieckman procedure suffers from several undesirable aspects. As with the Evans route, the Dieckmann procedure requires the side chain to be changed after the [2+2] cycloaddition reaction to form the azetidinone. Resolution limits the potential overall yield because half of the key intermediate azetidinone must be discarded. Also, the necessity of changing the ester protective groups (from methyl to p-nitrobenzyl) adds steps and decreases efficiency of the process.

There has remained a need for a simplified chiral method of preparing carbacephems. The present invention satisfies this need by providing a synthesis route which is chiral, eliminates the need to change side chains, and yields the desired nucleus in high overall yield. These methods and new intermediate β-lactam containing compounds represent significant advances over the prior art.

SUMMARY OF THE INVENTION

Compositions useful as intermediates in the preparation of carbacephems, convertible to cephalosporin analogs, are described which are characterized by the presence of both a 7-amino protecting chiral auxiliary and a 2-carboxy protecting group on the base compound structure. Novel methods for the preparation of carbacephems are also described in which the amino and carboxy protecting groups are maintained on the molecule throughout much of the synthesis procedure.

It is an object of the present invention to provide novel compounds useful in the preparation of carbacephems.

A further object of the present invention is to provide simple, efficient and high yield methods for preparing chiral carbacephem compounds.

It is another object of the present invention to provide a synthesis route for the preparation of carbacephems which eliminates the need to perform chemical or enzymatic resolutions.

Further objects and advantages of the present invention will be apparent from the description which follows.

DESCRIPTION OF THE PREFERRED EMBODIMENT

For the purposes of promoting an understanding of the principles of the invention, reference will now be made to the embodiments described herein. It will nevertheless be understood that no limitation of the scope of the invention is thereby intended, such alterations, modifications and further applications of the principles of the invention being contemplated as would normally occur to one skilled in the art to which the invention relates.

The present invention provides novel compounds and methods which permit the ready preparation of cephalosporin analogs. The compounds and methods are particularly useful, for example, in the preparation of molecules including the carbacephem nucleus, i.e. the 1-carba(1-dethia)-3-cephem-4-carboxylic acids, also known as 1-carbacephalosporins or cephalosporin analogs:

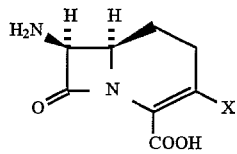

The invention is especially useful in preparing the 3-substituted derivatives, such as 3-chloro-1-carba(1-dethia)-3-cephem-4-carboxylic acids.

The present invention relies upon a synthesis route characterized by a limited number of steps and high yield. The process utilizes a chiral auxiliary side chain which protects the 7-amino group of the 1-carbacephem, and which is carried through the synthesis without change. The 2-carboxy protective group, which may be a methyl ester function or other group, e.g. p-nitrobenzyl, may also be carried through the process without change. Surprisingly, it has been determined that these protective groups may be removed at a point late in the reaction sequence, which conveniently yields the desired product.

This process combines aspects of the prior art Evans and Dieckmann routes, but differs significantly in the use of protective side chains which are not changed during the process. In contrast to the prior art procedures, the chiral auxiliary is retained as the side chain through to the final step in preparing the carbacephem. Heretofore it has not been considered possible to remove the chiral auxiliary from the carbacephem without also removing most 3-substituted functions, since birch reduction was being used to give the carbacephem nucleus. The present invention overcomes this problem, and the chiral auxiliary side chain and methyl ester function may be carried through without change.

The compounds and processes of the present invention are exemplified by the following methodology. The synthesis begins with the formation of an azetidin-2-one ester of the formula (I):

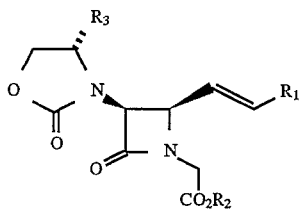

in which $R_1$, $R_2$ and $R_3$ are as defined hereafter. The oxazolidone group, also referred to herein as the Evans chiral auxiliary, serves as an amino protecting group during subsequent steps of the synthesis, until cleaved at the end of the methodology. Similarly, the $R_2$ group forming the ester functions as a carboxy protecting group during subsequent steps, and is removed near the end of the overall synthesis.

The azetidinone ester (I) is obtained by the 2+2 cycloaddition of a 4(S)-aryloxazolidin-2-one-3-ylacetyl halide having the formula (1):

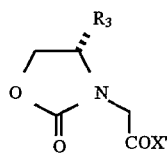

in which X' is halogen, and an imine ester having the formula (2):

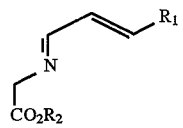

The preparation of the acetyl halide and similar imines, as well as the general cylcoaddition procedure, are generally described in U.S. Pat. No. 4,665,171, issued to Evans et al. on May 12, 1987, and the pertinent portions thereof are hereby incorporated by reference.

The 2-vinyl azetidin-2-one ester (I) is then hydrogenated to give the 2-alkyl azetidin-2-one ester having the formula (II):

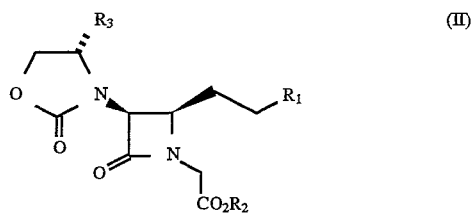

This compound (II) is in turn converted to the 2-carboxylic acid ($R_1$=COOH), and then to the 2-carboxylate (e.g., $R_1$=$CO_2Ph$, in which Ph=phenyl).

Cyclization of the 2-carboxylate yields the 4,6-bicyclo compounds having the formula (III):

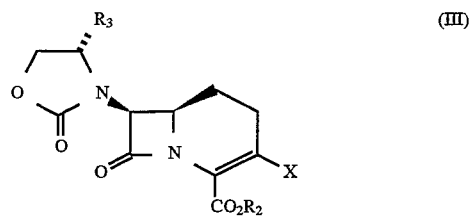

in which $R_2$ and $R_3$ are unchanged from the prior compounds, and in which X=OH.

The 3-position hydroxyl group is then replaced, e.g., with halogen, and the product converted to, for example, the loracarbef nucleus of the formula:

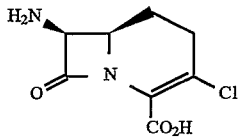

General Synthesis Process

It is an aspect of the present invention that the amino protecting group (Evans chiral auxiliary) and the carboxy protecting group are both removable from the root compound late in the synthesis. This contributes substantially to the efficiency and yield of the overall procedure.

In the preferred method depicted below, therefore, the amino protecting chiral auxiliary and the carboxy protecting group are present upon formation of the azetidinone ester. The synthesis proceeds through to the preparation of the 3-substituted, 7-amino protected and 2-carboxy protected, bicyclo compound, which is subsequently converted to the carbacephem. The specific intermediate steps leading to the 3-substituted bicyclo may proceed by various routes and chemistries, provided the amino protecting and carboxy protecting groups are retained on the 3-substituted bicyclo product. An exemplary and preferred synthesis approach is shown below:

Reaction Scheme I - Generic Synthesis

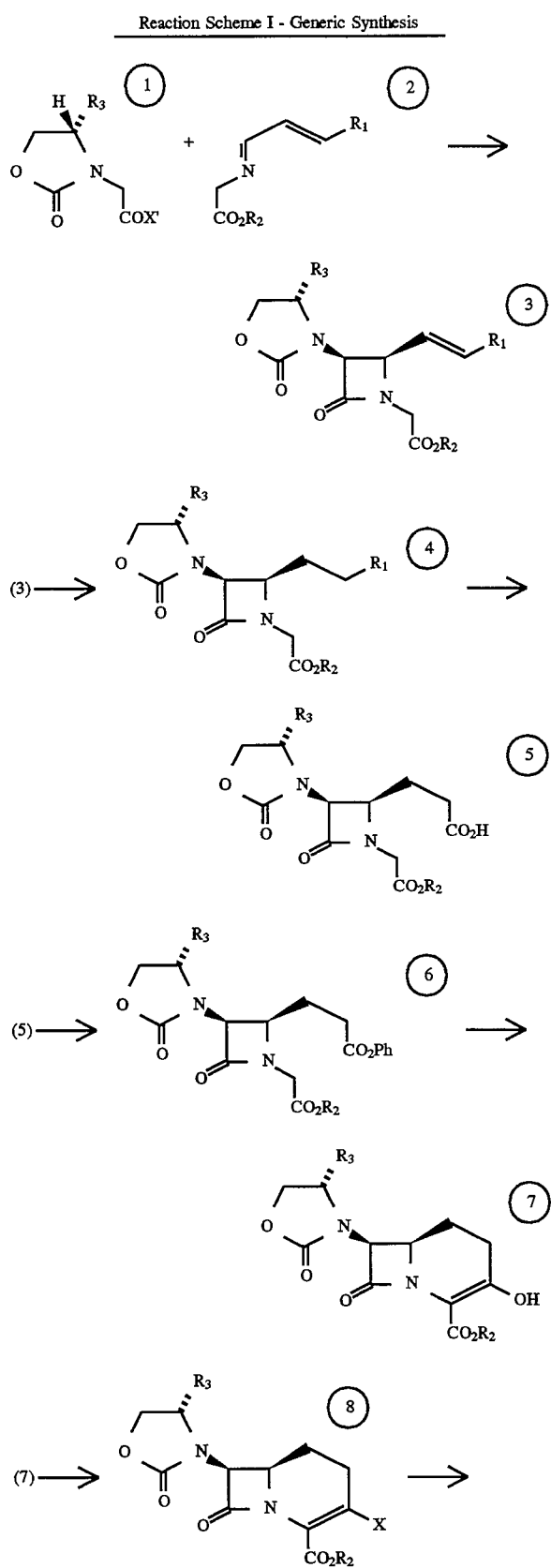

-continued
Reaction Scheme I - Generic Synthesis

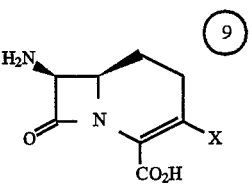

As previously indicated, the azetidin-2-one esters (3) are prepared by the 2+2 cycloaddition of a 4(S)-aryloxazolidin-2-one-3-ylacetyl halide (1) and an imine ester (2). The acetyl halide may be converted in situ with a trialkylamine to the corresponding homochiral ketene. The ketene and imine upon cycloaddition provide the azetidinone. Alternatively, the ketene can be generated with the anhydride of the oxazolidinone acetic acid and trifluoroacetic acid, or with phosphoryl chloride or phosphoryl bromide, or alkyl chloroformate.

The 4(S)-aryloxazolidin-2-one-3-ylacetyl halide (1) used in the cycloaddition may be represented by the formula (1) in which $R_3$ is for example phenyl, $C_1$-$C_4$ alkylphenyl, halophenyl, $C_1$-$C_4$ alkoxyphenyl, naphthyl, thienyl, furyl, benzothienyl or benzofuryl; and X' is chloro, bromo, trifluoroacetoxy or —OP(=O)X"$_2$ wherein X" is halogen. The oxazolidinone serves as an amino protecting group here and through the synthesis to the eventual bicyclo compounds, e.g., compounds 7 and 8.

Preparation of the acetyl halide may be accomplished, for example, in accordance with the procedure described in the Evans U.S. No. Patent 4,665,171, incorporated herein by reference. In summary, the acetyl halide is obtained from an L-arylglycine which is first converted to the carbamate and then reduced to provide the L-alcohol. The L-alcohol is then cyclized to the (S)-4-aryloxazolidin-2-one, which is subsequently N-alkylated with a haloacetic acid ester, the ester deesterified, and the acid converted to the acetyl halide.

The imine ester may be represented by the formula (2) in which $R_1$ is selected from the group consisting of 2-furyl, naphthyl, phenyl and phenyl substituted with 1, 2 or 3 substituents selected from $C_1$-$C_6$ alkyl, $C_1$-$C_6$ alkoxy, $C_1$-$C_6$ alkylthio, nitro, halo, carboxy and amido; and $R_2$ is a carboxy protecting group, e.g., methyl, p-nitrobenzyl, phenyl, $C_1$-$C_4$ alkylphenyl, $C_1$-$C_4$ alkoxyphenyl, halophenyl or others listed hereafter.

Preparation of the imine ester may be accomplished, for example, by the procedure described in the Evans U.S. Pat. No. 4,665,171, incorporated herein by reference. For example, a 3-arylacrolein may be condensed in a suitable solvent with a carboxy protected glycine. The condensation proceeds rapidly in the presence of a drying agent or during azeotropic removal of the water produced in the reaction.

The term "carboxy protecting group" used herein refers to a moiety which forms an ester derivative of the carboxylic acid group. The species of carboxy protecting group employed in the present invention is not critical, so long as the derivatized carboxylic acid is stable to the conditions of subsequent reaction(s) on other positions of the molecule, and the group can be removed at an appropriate subsequent step without disrupting the remainder of the molecule.

Carboxy protecting groups similar to those used in the cephalosporin, penicillin and peptide arts can be used to protect the carboxy substituents of the compounds provided herein. The preferred carboxy protecting groups are methyl and p-nitrobenzyl (PNB). Numerous other carboxy protecting groups have been previously identified, and may include benzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. See also U.S. Pat. No. 4,734,494 (column 2, line 56 to column 3, line 17), issued to Hirata et al.

It is desirable that the $R_2$ protecting group remain attached to the molecule throughout subsequent manipulations, although it is within the scope of the present invention that the $R_2$ group could be substituted during intermediate steps of the synthesis. It is, however, a further aspect of the present invention that the carboxy protecting group is removed in the final cleavage step(s) resulting in formation of the desired carbacephem.

The present invention provides compounds having at the same time both the amino protecting Frans chiral auxiliary and the carboxy protecting group $R_2$. Compounds of this type, such as the azetidin-2-ones esters, have been found to be especially desirable as they permit the production of target compounds in high yield and with reduced numbers of steps. The advantage is heightened when both of these protecting moieties are retained throughout the synthetic procedure. It is therefore a particular aspect of the present invention that both moieties are placed onto the root of the compound and are retained during subsequent manipulative steps, such as hydrogenation, chlorination, etc. In addition, as is later described, it is a feature of the present invention that the development of a one or two-step removal of the protecting groups, such as by reaction with trimethylsilyl iodide, greatly facilitates the preparatory process.

The produced 2-vinyl azetidin-2-one ester (3) is then hydrogenated to give the 2-alkyl azetidin-2-one ester (4). Reduction of the 2-vinyl double bond proceeds readily in solution with soluble or insoluble hydrogenation catalysts, such as Pd/C catalyst or other insoluble or soluble hydrogenation catalyst, with the introduction of hydrogen gas. Preferably, this reaction proceeds without cleavage of the $R_2$ carboxy protecting group. Further, the amino protecting chiral auxiliary remains intact. Removal or substitution of these two groups is therefore avoided, and the overall synthesis is consequently made simpler and more efficient.

The $R_1$ group is subsequently converted to COOH (5), and then to the carboxylate ester (e.g., COOPh) (6). These steps may proceed, for example, by ozonolysis of an $R_1$ furyl moiety to yield the carboxylic acid which is then converted to the ester, e.g. by reaction with phenol, thiophenol, 1,3-dicyclohexylcarbodiimide and a catalytic amount of 4-dimethylaminopyridine. These chemistries are known in the art, being described for example in B. G. Jackson et al., "Synthesis of Carbacephem Antibiotics: Synthesis Via Dieckmann Reaction Using Phenyl Esters to Direct the Regioselectivity of the Cyclization," Tetrahedron Letters, Vol. 31, No. 44, pp. 6317–6320 (1990), which is hereby incorporated by reference.

Cyclization of the diester (6) to the β-ketoester (7) may also be effected using chemistries described in the art. Jackson et al., in the foregoing "Synthesis of Carbacephom Antibiotics," describe such a cyclization with lithium hexamethyldisilazide or potassium tert-butoxide in tetrahydrofuran at −78° C. Subsequent replacement of the 3-hydroxy group is straightforward to yield the desired 3-substituted (typically halogenated) product (8).

The synthesis proceeds thereafter with cleavage of the amino protecting and carboxy protecting groups. The preferred method to cleave the amino protecting chiral auxiliary and the carboxy protecting group is by reaction with trimethylsilyl iodide (TMSI). As demonstrated in the Examples hereafter, these protective groups function in the intermediate steps to protect the desired 7-amino and 2-carboxy substituents of the carbacephem product, and are readily removed with TMSI chemistry. However, carboxy protecting groups such as methyl or p-nitrobenzyl may also be removed by TMSI and have properties which make them particularly preferred.

Conversion of the 3-substituted, e.g. 3-chloro, compound (8) to the carbacephem (9) proceeds conveniently with TMSI chemistry. With methyl as the carboxy protecting group $R_2$, reaction with TMSI removes both the chiral auxiliary and the $R_2$ methyl, yielding the carbacephem (9). For non-methyl moieties as the carboxy protecting group, two alternate two-step procedures may be followed. In the preferred route, the carboxy protecting group, e.g. p-nitrobenzyl, is removed to yield the 2-carboxylic acid. Reaction of the carboxylic acid with TMSI then produces the carbacephem (9). In an alternate route, the chiral auxiliary is first cleaved with TMSI to provide the 7-amino compound, which is subsequently converted to the carbacephem by removal of the carboxy protecting group.

Compounds of the types I, II and III, which include both the amino protecting chiral auxiliary and the carboxy protecting group, have not been previously known. These compounds permit the ready preparation of a variety of useful materials with high yield.

The present invention thus provides novel compounds having the formula (I):

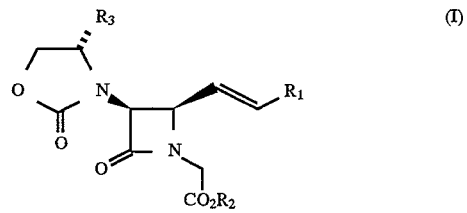

in which $R_1$ is selected from the group consisting of 2-furyl, naphthyl, phenyl and phenyl substituted with 1, 2 or 3 substituents selected from $C_1$–$C_6$ alkyl, $C_1$–$C_6$ alkoxy, $C_1$–$C_6$ alkylthio, nitro, halo, carboxy and amido, with the 2-furyl substituent being preferred. $R_2$ may be hydrogen or a carboxy protecting group as previously defined, and preferably is methyl or p-nitrobenzyl. $R_3$ is selected from the group consisting of phenyl, $C_1$–$C_4$ alkylphenyl, halophenyl, $C_1$–$C_4$ alkoxyphenyl, naphthyl, thienyl, furyl, benzothienyl and benzofuryl, and is most preferably phenyl. As described in the examples hereafter, a particularly preferred compound is one in which $R_1$ is 2-furyl, $R_2$ is methyl, and $R_3$ is phenyl.

Also provided by the present invention are compounds of the formula (II):

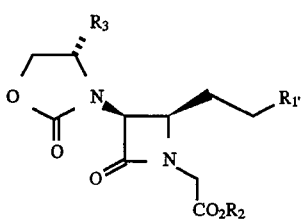

(II)

in which $R_1$, is selected from the group consisting of 2-furyl, naphthyl, phenyl, phenyl substituted with 1, 2 or 3 substituents selected from $C_1$–$C_6$ alkyl, $C_1$–$C_6$ alkoxy, $C_1$–$C_6$ alkylthio, nitro, halo, carboxy, carboxylic acid and amido, and a carboxylic acid derivative having a leaving group. The term "leaving group" is used herein in the conventional manner to refer to a substituent which is displaced from the molecule during a chemical reaction. Such a carboxylate derivative with a leaving group may be defined herein as being selected from $COOR_4$ and $COSR_4$, in which $OR_4$ and $SR_4$ are leaving groups and in which $R_4$ is selected from $C_1$–$C_6$ alkyl, $C_2$–$C_6$ alkenyl, phenyl or phenyl substituted with 1, 2 or 3 substituents such as $C_1$–$C_6$ alkyl, $C_1$–$C_6$ alkoxy, $C_1$–$C_6$ alkylthio, nitro, halo, carboxy, amido and the like, and related substituents. Preferred $R_1'$ groups are 2-furyl, carboxyl and phenylcarboxyl. $R_2$ is a carboxy protecting group, preferably methyl or p-nitrobenzyl (PNB). $R_3$ is selected from the group consisting of phenyl, $C_1$–$C_4$ alkylphenyl, halophenyl, $C_1$–$C_4$ alkoxyphenyl, naphthyl, thienyl, furyl, benzothienyl and benzofuryl, and preferably comprises phenyl.

In accordance with the Examples hereafter, preferred compounds of the formula II are the following:

| Compound No. | $R_1'$ | $R_2$ | $R_3$ |
| --- | --- | --- | --- |
| 4a | 2-furyl | methyl | phenyl |
| 4b | 2-furyl | PNB | phenyl |
| 4c | 2-furyl | H | phenyl |
| 5a | COOH | methyl | phenyl |
| 5b | COOH | PNB | phenyl |
| 6a | COOPh | methyl | phenyl |
| 6b | COOPh | PNB | phenyl |

Further novel compounds of the present invention include compounds of the formula (III):

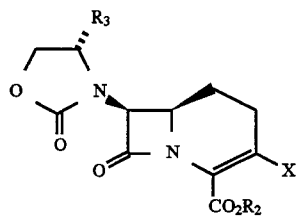

(III)

in which $R_2$ is a carboxy protecting group as previously defined, preferably methyl or p-nitrobenzyl, or is hydrogen. $R_3$ is selected from the group consisting of phenyl, $C_1$–$C_4$ alkylphenyl, halophenyl, $C_1$–$C_4$ alkoxyphenyl, naphthyl, thienyl, furyl, benzothienyl and benzofuryl, and is preferably phenyl.

The three position substituent X is selected from a variety of substituents known to yield useful carbacephems. In particular, X is selected from the group consisting of hydroxyl, halo, $C_1$–$C_6$ alkyl, $C_1$–$C_6$ substituted alkyl, $C_1$–$C_4$ alkoxy, $C_1$–$C_4$ alkylthio, trifluoromethyl, $C_2$–$C_6$ alkenyl, $C_2$–$C_6$ substituted alkenyl, $C_2$–$C_6$ alkynyl, $C_2$–$C_6$ substituted alkynyl, phenyl, substituted phenyl, $C_1$–$C_6$ alkyloxymethyl, phenyl-$C_1$–$C_6$ alkyloxymethyl, tri($C_1$–$C_6$) alkylsilyloxymethyl, trifluoromethylsulfonyloxy, nitrile and phenoxy.

As used herein, halogen includes bromo, chloro, iodo and fluoro. $C_1$–$C_4$ alkoxy refers to such groups as methoxy, ethoxy, propoxy and butyloxy. $C_1$–$C_4$ alkylthio includes methylthio, ethylthio, t-butylthio and like groups.

$C_1$–$C_6$ alkyl refers to the straight and branched chain alkyl groups such as methyl, ethyl, n-propyl, isopropyl, n-butyl, t-butyl, n-pentyl, n-hexyl, 3-methylpentyl, and like alkyl groups. $C_1$–$C_6$ substituted alkyl includes $C_1$–$C_6$ alkyls substituted with cyano, carboxy, halogen, amino, $C_1$–$C_4$ alkoxy, $C_1$–$C_4$-alkylthio, trifluoromethyl and trifluoromethylthio. $C_1$–$C_6$ alkyl substituted by cyano refers to cyanomethyl, cyanoethyl, 4-cyanobutyl, and the like; $C_1$–$C_6$ alkyl substituted by carboxy refers to such groups as carboxymethyl, 2-carboxyethyl, 2-carboxypropyl, 4-carboxybutyl, 5-carboxypentyl, and the like; $C_1$–$C_6$ alkyl substituted by halogen refers to chloromethyl, bromomethyl, 2-chloroethyl, 1-bromoethyl, 4-chlorobutyl, 4-bromopentyl, 6-chlorohexyl, 4-fluorobutyl, 3-fluoropropyl, fluoromethyl, and the like; $C_1$–$C_6$ alkyl substituted by amino refers to such groups as 2-aminoethyl, aminomethyl, 3-aminopropyl and 4-aminobutyl; $C_1$–$C_6$ alkyl substituted by $C_1$–$C_4$ alkoxy refers to methoxymethyl, 2-methoxyethyl, 2-ethoxyethyl, ethoxymethyl, 3-propoxypropyl, 3-ethoxybutyl, 4-t-butyloxybutyl, 3-methoxypentyl, 6-methoxyhexyl, and like groups; $C_1$–$C_6$ alkyl substituted by $C_1$–$C_4$ alkylthio refers to such groups as for example methylthiomethyl, 2-methylthioethyl, 2-ethylthiopropyl, 4-methylthiobutyl, 5-ethylthiohexyl, 3-t-butylthiopropyl, and like groups; $C_1$–$C_6$ alkyl substituted by trifluoromethyl is exemplified by 2,2,2-trifluoroethyl, 3,3,3-trifluoropropyl, 4,4,4-trifluorobutyl, and the like; and $C_1$–$C_6$ alkyl substituted by trifluoromethylthio refers to, for example, trifluoromethylthiomethyl, 2-trifluoromethylthioethyl, 2-trifluoromethylthiopropyl, 4-trifluoromethylthiobutyl, 5-trifluoromethylthiohexyl, and like $C_1$–$C_6$ alkyl substituted groups.

$C_2$ to $C_6$ alkenyl refers to straight and branched olefins. Examples of the term $C_2$ to $C_6$ alkenyl include ethenyl, 1-propenyl, 2-propene-1-yl, 1-butene-1-yl, 2-butene-1-yl, 3-butene-1-yl, 1-pentene-1-yl, 2-pentene-1-yl, 3-pentene-1-yl, 4-pentene-1-yl, 1-hexene-1-yl, 2-hexene-1-yl, 3-hexene-1-yl, 4-hexene-1-yl, 5-hexene-1-yl, isopropene-1-yl, isobutenyl, isopentenyl, isohexenyl and the like. A preferred subgroup of the term $C_2$ to $C_6$ alkenyl is a group of the formula $C_3$ to $C_6$ alkenyl.

$C_2$ to $C_6$ substituted alkenyl refers to a $C_2$ to $C_6$ alkenyl group substituted by one or more halogen, hydroxy, protected hydroxy, nitro or trihalomethyl groups. It will, of course, be appreciated that a free hydroxy group may need to be protected during the course of the process as taught herein. Preferred $C_2$ to $C_6$ substituted alkenyl groups are (Z)-3,3,3-trifluoro-1-propene-1-yl and (Z)-1-propene-1-yl.

$C_2$–$C_6$ alkynyl refers to straight and branched acetylenic groups. Examples of the term $C_2$ to $C_6$ alkynyl include ethynyl, 1-propyne-1-yl, 2-propyne-1-yl, 1-butyne-1-yl, 2-butyne-1-yl, 3-butyne-1-yl, 1-pentyne-1-yl, 2-pentyne-1-yl, 3-pentyne-1-yl, 4-pentyne-1-yl, 1-hexyne-1-yl, 2-hexyne-1-yl, 3-hexyne-1-yl, 4-hexyne-1-yl, 5-hexyne-1-yl, 2-methyl-2-propyne-1-yl, 2-methyl-4-propyne-1-yl, 2-methyl-3-pentyne-1-yl, 2-methyl-3-butyne-1-yl and the like.

$C_2$ to $C_6$ substituted alkynyl refers to a $C_2$ to $C_6$ alkynyl group substituted by one or more of halogen, hydroxy, protected hydroxy, nitro or trihalomethyl.

Examples of the term $C_1$ to $C_6$ alkyloxymethyl include methyloxymethyl, ethyloxymethyl, n-propyloxymethyl, n-butyloxymethyl, n-pentyloxymethyl, n-hexyloxymethyl, isopropyloxymethyl, isobutyloxymethyl, isopentyloxymethyl, isohexyloxymethyl and the like. Examples of the term phenyl $C_1$ to $C_6$ alkyloxymethyl include benzyloxymethyl, (2-phenyl)ethyloxymethyl, (3-phenyl)-n-propyloxymethyl, (4-phenyl)-n-butyloxymethyl, (5-phenyl)-n-pentyloxymethyl, (6-phenyl)-n-hexyloxymethyl, (2-phenyl)(2-methyl)ethyloxymethyl, (3-phenyl(3-methyl)-n-propyloxymethyl and the like.

Substituted phenyl refers to a phenyl group substituted with a and/or a', wherein a and a' independently are hydrogen, halogen, hydroxy, $C_1$–$C_4$ alkoxy, $C_1$–$C_4$ alkanoyloxy, $C_1$–$C_4$ alkyl, $C_1$–$C_4$ alkylthio, amino, mono- or di($C_1$–$C_4$ alkyl)amino, $C_1$–$C_4$ alkanoylamino, $C_1$–$C_4$ alkylsulfonylamino, carboxy, carbamoyl, hydroxymethyl, aminomethyl, or carboxymethyl. Examples of such substituted phenyl groups are halophenyl such as 4-chlorophenyl, 3-bromophenyl, 2-fluorophenyl, 2,4-dichlorophenyl, and 3,5-dichlorophenyl; hydroxyphenyl such as 2-hydroxyphenyl, 3-hydroxyphenyl, 4-hydroxyphenyl, 2,4-dihydroxyphenyl, and 3,4-dihydroxyphenyl, alkoxyphenyl, such as 2,6-dimethoxyphenyl, 4-methoxyphenyl, 3-ethoxyphenyl, 3,4-dimethoxyphenyl, 4-t-butyloxyphenyl, 4-methoxy-3-ethoxyphenyl, and 4-n-propoxyphenyl; alkanoyloxyphenyl such as 2-acetoxyphenyl, 4-propionoxyphenyl, 4-formyloxyphenyl, 4-acetoxyphenyl, 3-butyryloxyphenyl, and 3-acetoxyphenyl; alkylphenyl such as 4-methylphenyl, 2-methylphenyl, 2,4-dimethylphenyl, 3-t-butylphenyl, 4-ethylphenyl, 4-ethyl-3-methylphenyl, and 3,5-dimethylphenyl; alkylthiophenyl such as 4-methylthiophenyl, 3-n-butylthiophenyl, 2-ethylthiophenyl, 3,4-dimethylthiophenyl, and 3-n-propylthiophenyl; aminophenyl such as 2-aminophenyl, 4-aminophenyl, 3,5-diaminophenyl, and 3-aminophenyl; alkanoylamino such as 2-acetylamino, 4-acetylamino, 3-propionylamino, and 4-butyrylamino; alkylsulfonylamino such as 3-methylsulfonylamino, 4-methylsulfonylamino, 3,5-(dimethylsulfonylamino)phenyl, 4-n-butylsulfonylaminophenyl, and 3-ethylsulfenylaminophenyl; carboxyphenyl such as 2-, 3-, or 4-, carboxyphenyl, 3,4-dicarboxyphenyl, and 2,4-dicarboxyphenyl; carbamoylphenyl such as 2-carbamoylphenyl, 2,4-dicarbamoylphenyl, and 4-carbamoylphenyl; hydroxymethylphenyl such as 4-hydroxymethylphenyl and 2-hydroxymethylphenyl; aminomethylphenyl such as 2-aminomethylphenyl and 3-aminomethylphenyl; and carboxyphenyl such as 2-carboxymethylphenyl, 4-carboxymethylphenyl, and 3,4-dicarboxymethylphenyl; and the substituted phenyl groups bearing different substituents such as 4-chloro-3-methylphenyl, 4-fluoro-3-hydroxyphenyl, 3,4-dichloro-4-hydroxyphenyl, 4-hydroxy-3-chlorophenyl, 4-hydroxy-3-methylphenyl, 4-ethyl-3-hydroxyphenyl, 4-methoxy-3-hydroxyphenyl, 4-t-butyloxy-2-hydroxyphenyl, 4-acetylamino-3-methoxyphenyl, 3-amino-4-ethylphenyl, 2-aminomethyl-4-chlorophenyl, 2-hydroxymethyl-3-methoxyphenyl, 2-hydroxymethyl-4-fluorophenyl, 2-acetoxy-4-aminophenyl, 4-acetoxy-3-methoxyphenyl, 3-isopropylthio-4-chlorophenyl, 2-methylthio-4-hydroxymethylphenyl, 4-carboxy-3-hydroxyphenyl, 4-ethoxy-3-hydroxyphenyl, 4-methylsulfonylamino-2-carboxyphenyl, 4-amino-3-chlorophenyl, and 2-carboxymethyl-4-hydroxyphenyl.

As shown in the Examples hereafter, preferred compounds of the formula III are the following:

| Compound No. | $R_2$ | $R_3$ | X |
|---|---|---|---|
| 7a | methyl | phenyl | OH |
| 7b | PNB | phenyl | OH |
| 8a | methyl | phenyl | Cl |
| 8b | PNB | phenyl | Cl |
| 8c | H | phenyl | Cl |

The carbacephems prepared in accordance with the methods of this invention are known to be useful as intermediates in the preparation of various specific acylated compounds, i.e. cephalosporin analogs, useful as antibacterial agents. See, e.g., U.S. Pat. No. 4,335,211, issued to Hashimoto et al. on Jun. 15, 1982; and U.S. Pat. No, 4,734,494, issued to Hirata et al. on Mar. 29, 1988, both of which are hereby incorporated by reference. Conversion to the analogs may be performed in conventional fashions, such as by selective acylation in accordance with the methods of the Hashimoto U.S. Pat. No. 4,335,211.

The following Examples further exemplify the compounds and methods of the present invention. However, these Examples are illustrative only, and are not limiting to the scope of the inventions herein.

Preparation of Carbacephems Using Methyl as the Carboxy Protecting Group

In Examples 1–7 are described the compositions and methods for preparing carbacephems using methyl as the carboxy protecting group. The reaction scheme is illustrated below:

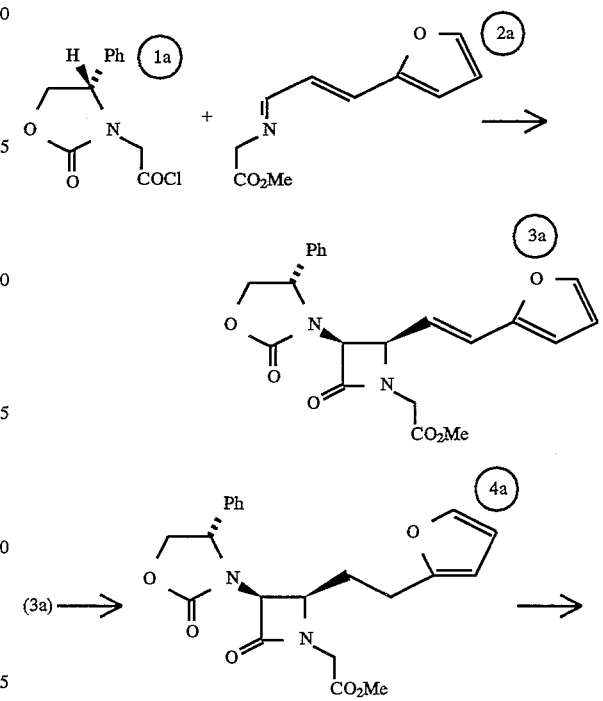

-continued
Reaction Scheme II - Methyl Carboxy Protecting Group

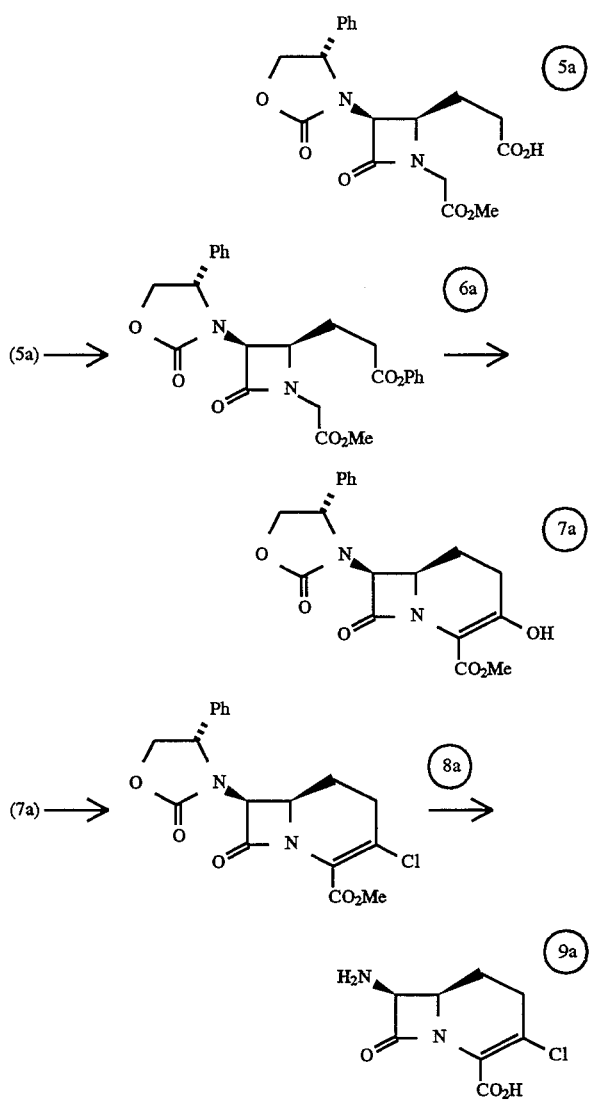

EXAMPLE 1

The acid chloride (1a) (approximately 325 mM) was cooled to –40° C. and 2 molar equivalents (eq.) of triethylamine (TEA) (90.4 ml, 650 mM) were added dropwise over 20 min. The mixture was stirred 10 min. and the Schiff base methyl ester (2a) solution (63 g, 326 mM of ester in 360 ml $CH_2Cl_2$) was added over 25 min. After another 60 min., and with the temperature having risen to –30° C., HPLC showed residual Schiff base. The mixture was stirred further, allowing the temperature to rise to –20° C. An additional 45.2 ml (325 mM) of TEA in 90 ml $CH_2Cl_2$ was added over 15 minutes. HPLC then showed 81% product. The temperature was allowed to rise to –10° C., and HPLC showed 88% product. The temperature was held at –10° C., and the reaction finished in about 60 min. at 94% product. The reaction mixture was quenched with 500 ml 1N HCl, with the temperature rising to 10° C. The product solution was separated and washed successively with 50 ml brine, 1000 ml 3% $NaHCO_3$, and 50 ml brine, then dried with $Na_2SO_4$ and refrigerated overnight. The solution was filtered and employed in the subsequent hydrogenation reaction of Example 2. The dried solution, by HPLC, did not deteriorate overnight under refrigeration.

EXAMPLE 2a

Hydrogenation of the methyl ester (3a) (128.8 g in 1300 ml $CH_2Cl_2$) was carried out at room temperature and atmospheric pressure with hydrogen balloons and about 5% by weight of Pd/C catalyst (6.5 g). The procedure included purging the reaction vessel with $N_2$, applying the $H_2$ balloon with closed stopcock, applying partial vacuum to the boiling point of the $CH_2Cl_2$, closing the vacuum, opening the $H_2$ balloon stopcock, and then repeating this degassing procedure as needed. The reaction was followed by HPLC in MeOH/$H_2O$ (50/50), which gave the starting material at 5.45 min. and the product at 6.15 min. The hydrogenated (reduced) product (4a) had about 1% of the UV absorbance of the starting material at 254 nm, and consequently one essentially monitored the disappearance of the starting material. One drop of the filtered solution was diluted with 1 ml ACN/$H_2O$/$H_3PO_4$ (50/50/0.2%). HPLC showed a clean reduction, complete in about 7½ hours. The Pd/C catalyst was filtered on a washed Hyflo pad and refrigerated overnight. The $CH_2Cl_2$ was evaporated to 212 g syrup, and was seeded to crystallize. Ether (400 ml) was slowly added to slurry the crystals, and the slurry was then filtered with a 200 ml ether wash. The first product (A) was vacuum dried at 50° C. to 101.0 g, a yield of 78%. The filtrate was evaporated to 27.5 g of oil, which was crystallized with ether and seeding. The product (B) was filtered with an ether wash to obtain 2.9 g of product, a yield of 2.2%. Total yield was about 80% over the two steps. Concentrated samples of (A) and (B) were run on HPLC in ACN/$H_2O$/$H_3PO_4$ (44/56/0.2%), and large peaks for the product (4a) were obtained. IR showed the β-lactam at 1758.9 $cm^{-1}$. Sp. rot. at 589 nm ($CHCl_3$) was +55.89 deg. Analysis calculated for $C_{21}H_{22}N_2O_6$: C, 63.31; H, 5.57; N, 7.03. Found: C, 63.08; H, 5.37; N, 7.00. NMR ($CDCl_3$) δ 1.72 (m, 2), 2.64 (t, 2), 3.48 (d, 1), 3.68 (s, 3), 3.91 (q, 1), 4.26 (d, 1), 4.30 (dd, 1), 4.64 (d, 1), 4.72 (t, 1), 4.94 (dd, 1), 5.98 (d, 1), 6.29 (dd, 1), 7.30 (d, 1), 7.40 (s, 5).

EXAMPLE 2b

Hydrogenation on a lot of the 2+2 product (3a) which was isolated as a solid was again run at room temperature and atmospheric pressure with hydrogen balloons and about 2% by weight Pd/C catalyst (as per Example 2a). The reaction mixture comprised 110 g (277 mM) of the methyl ester (3a) in 1100 ml $CH_2Cl_2$ and 2.2 g of 5% Pd/C catalyst. This was carefully degassed by pulling a partial vacuum (until $CH_2Cl_2$ began to boil), shutting off the vacuum, opening the $H_2$ stopcock, and repeating this procedure before leaving the reaction vessel open to the $H_2$ balloon. HPLC in MeOH/water (50/50) showed a clean reaction with disappearance of starting material over about 6¼ hours. The product was only slightly UV absorbing (about 1/100 that of the starting material) and therefore appeared as a tiny blip on HPLC. The Pd/C catalyst was filtered on the Hyflo, with a 200 ml $CH_2Cl_2$ wash, and evaporated to 206 g syrup. This syrup was quickly diluted in 60 ml ether and stirred magnetically to crystallize. Ether (340 ml) was slowly added and the mixture filtered with an ether wash. The precipitate (4a) was vacuum dried at 50° C. to 86.6 g (A). Yield was approximately 78.5%. After the filtrate sat 3 days at room temperature, it was decanted from an oily precipitate and evaporated to 227 g crystals and oil. This material was slurried with 50 ml ether/isopropyl alcohol (3/1), and filtered with a wash of the same solution. The product (4a) was dried to 1.5 g (B). The yield was about 1.4%. Total isolated yield was about 80%. NMR's of (A) and (B) in $CDCl_3$ were consistent with desired product.

EXAMPLE 3

Conversion of the furan (4a) to the carboxylic acid (5a) was accomplished by ozonolysis. The furan (4a) (7.97 g 20 mM) was combined with 144 ml $CH_2Cl_2$ and 16 ml MeOH and cooled in dry ice to −65° C. The ozonolysis proceeded with addition of $O_3$ until 4 minutes after the appearance of a blue color indicating the presence of an excess of ozone. The excess ozone was purged with $O_2$, followed by $N_2$. $H_2O_2$ (6.8 ml of 30% solution) was added, the cold bath removed, and the mixture warmed to room temperature in 30 minutes. After about 2 hours at room temperature, HPLC showed a good ozonolysis. The mixture was washed with 2×150 ml saturated brine and stored at room temperature overnight. The solution was treated with solid $NaHSO_3$ (1.04 g, 10 mM) and stirred until negative to a starch-iodide paper test. $Na_2SO_4$ was added to dry. The $NaHSO_3$ and $Na_2SO_4$ were filtered out and the product solution evaporated to 9.2 g foam which gave crystals upon addition of EtOAc (25 ml). The crystallization mixture was diluted with 3 volumes of ether and stirred 2 hours. Filtration with 25 ml of EtOAc:ether (1:4) wash followed by ether yielded 6.35 g white solid carboxylic acid (5a). Yield 84%. NMR ($CDCl_3$): δ 1.58 (m, 1), 1.81 (m, 1), 2.38 (t, 2), 3.64 (d, 1), 3.71 (s, 3), 3.94 (m, 1), 4.28 (d, 1), 4.34 (dd, 1), 4.69 (d, 1), 4.77 (t, 1), 5.04 (dd, 1), 7.43 (s, 5). Analysis calculated for $C_{18}H_{20}N_2O_7$: C, 57.44; H, 5.37; N, 7.44. Found: C, 56.84; H, 5.35; N, 7.04.

EXAMPLE 4

The phenyl ester (6a) preparation was run with the combination of 39 g (103.6 mM) of the carboxylic acid (5a) in 323 ml $CH_2Cl_2$ cooled to 0° C. TEA (14.43 ml, 103.6 mM) was added dropwise, and the mixture was cooled to −30° C. 2.53 g (20.7 mM) dimethylaminopyridine (DMAP) was then added, followed by the addition of 17.5 ml (139.2 mM) phenyl chloroformate. The bath temperature was then brought to 0° C. over 20 minutes. 1N HCl (124 ml) was added, and the solution was stirred to room temperature. The acid wash was separated, and HPLC showed that the DMAP and some phenol were present. The solution was washed with 200 ml $H_2O$, which removed the remainder of the DMAP and some of the phenol. It was then washed with 2×200 ml brine and dried with $MgSO_4$. HPLC showed product (6a) was about 74% and phenol was about 6%. Also present were three slow impurities but no starting material. The solution was evaporated to 53 g oil and placed in a freezer overnight, and was then employed as is in the subsequent ring closure reaction (Example 5a).

EXAMPLE 5a

The Dieckmann reaction was run on the oil (46.9 g, 103.6 mM) of Example 4 with four equivalents of sodium tertiary pentoxide (45.6 g, 414.4 mM) in 536 ml THF. After the ester 6a addition at −78° C., the mixture was stirred for 20 min. and 518 ml 1N HCl were added. The reaction exothermed to −5° C. and was stirred 5 min. to 0° C. pH=2. 518 ml brine was added and the organic layer was separated. The aqueous layer was back extracted with 322 ml $CH_2Cl_2$. The organic extracts were combined and a little more aqueous layer was separated out. This material was evaporated to about 500 ml vol. in the rotary evaporator, and then washed with 100 ml brine and dried with $Na_2SO_4$. The product crystallized during drying, and the $Na_2SO_4$ was therefore filtered with $CH_2Cl_2$ washes. 200 ml 2-butanol was added and the resulting mixture was evaporated to about 300 ml vol. Product was crystallizing. Another 200 ml 2-butanol was added and the mixture was evaporated to about 400 g slurry. 100 ml 2-butanol was added and the mixture was evaporated to about 427 g slurry, filtered at room temperature and washed with 100 ml 2-butanol, then ethyl ether. This product was vacuum dried at 40° C. overnight. The recovered product (A) weighed 24.11 g for an uncorrected yield of 65% over the two reactions. HPLC of (A) was excellent. The filtrate and washes were placed in a freezer overnight, and then (B) was filtered and washed with 2-butanol and ether. More crystals were present in the filtrate, so it was filtered (C), and the nearly white crystals were dried to 1.50 g, another 4% in yield. (B) was a sticky brown solid, so it was slurried with 30 ml THF to break it up, and 60 ml 2-butanol was added and the mixture was evaporated. The crystals were gummy, so the 2-butanol was evaporated to obtain a gum which broke up nicely with 20 ml EtOAc. Ether tended to gum the product, so it was filtered from EtOAc with an EtOAc wash of 10 ml. The resulting product was vacuum dried at 40° C. to (D) 0.72 g, another 2% in yield. Total isolated yield was 71%. HPLC's for (C) and (D) were good. NMR ($CDCl_3$): δ 1.52 (m, 1), 1.85 (m, 1), 2.33 (m, 2), 3.65 (m, 1), 3.84 (s, 3), 4.32 (dd, 1), 4.68 (d, 1), 4.74 (t, 1), 5.02 (dd, 1), 7.40 (m, 5), 11.28 (s, 1)

EXAMPLE 5b

The Dieckmann ring closure to form the enol (7a) was performed at room temperature on the phenyl ester (6a) (0.45 g, 1.0 mM) in 10 ml THF, combined with 0.93 g (2.1 mM) 55% NaH and 0.19 ml (2 mM) t-BuOH. A slow reaction to form $Na^+$OtBu took the temperature to 28° C. Ring closure was completed in less than 20 min. At 30 min., the mixture was quenched with excess AcOH (0.29 ml, 5 mM), showing very little exotherm. After stirring 5 min., 10 ml 2-butanol was added, and the mixture was then evaporated to a 6.2 g slurry (about 5 ml vol.). 1 ml $H_2O$ was added to dissolve any $Na^+$OAc, and the mix was then stirred 1 hour at room temperature and filtered. The precipitate was washed with 8 ml 2-butanol/$H_2O$ (5/1), and then $H_2O$. Filtration was slow. The cream colored product (7a) was vacuum dried for 24 hours at 45° C. to 0.25 g. Weight yield was about 70%. HPLC of the product (7a) showed only a trace of phenol. NMR ($CDCl_3$): δ 1.50 (m, 1), 1.84 (m, 1), 2.31 (m, 2), 3.64 (m, 1), 3.84 (s, 3), 4.31 (dd, 1), 4.68 (d, 1), 4.74 (t, 1), 5.02 (dd, 1), 7.39 (m, 5), 11.27 (s, 1).

EXAMPLE 6

A phosphite/$Cl_2$ reagent was prepared by combining 25 ml $CH_2Cl_2$ and 75 ml EtOAc, cooling the solution to −35° C., and simultaneously adding 5.26 ml (20 mM) triphenyl phosphite and $Cl_2$ gas, yielding a clear solution. To this solution was added 1.57 ml (20 mM) pyrimidine which gave an immediate precipitate, and then the enol (7a) (3.58 g, 10 mM) with 2 ml $CH_2Cl_2$. The temperature rose to 23° C. in less than 5 min. The mixture was stirred 6½ hours, and HPLC showed very little enol remaining, about 4%. The ratio of product ester to product acid was about 3.5 to 1. 10% by volume MeOH was added to convert the acid chloride or anhydride (which gives an acid product on HPLC if the sample sets for 15 min.) to the methyl ester, and conversion was complete in 30 min. $CH_2Cl_2$ (100 ml) wax added to facilitate separation of the layers, and the organic layer was then washed with 2×100 ml 1N HCl and with brine. The resulting material was dried with $Na_2SO_4$ and evaporated to 11.6 g residue. The product was crystallized by addition of 40 ml methyl t-butyl ether (MTBE), heating to boiling, and stirring to room temperature overnight. The product was filtered and washed with 25 ml MTBE, and vacuum dried at 45° C. for four days to yield 3.60 g of a beige solid methyl ester (8a). Weight yield was 95%. HPLC showed only 72% for a product (8a) yield of 69%. HPLC of the filtrate also showed some product. NMR (DMSO d-6) δ 1.97 (m, 2), 2.57 (m, 2), 3.70 (s, 3), 3.78 (m, 1), 4.10 (dd, 1), 4.49 (d, 1), 4.71 (t, 1), 5.00 (dd, 1), 7.38 (m, 5).

EXAMPLE 7

This procedure demonstrates a key aspect of the present invention. The methyl ester and the chiral auxiliary side chain are both cleaved via reaction of the methyl ester product (8a) with trimethylsilyl iodide (TMSI). The methyl ester (8a) (0.377 g, 1 mM) and 3.8 ml acetonitrile (ACN) were combined with 2.5 equivalents each of hexamethyldisilazane (HMDS) (0.53 ml) and TMSI (0.36 ml), and the reaction mixture was refluxed at about 80° C. After 1½ hours, deesterification was about 30% complete and the oxazolidinone ring opening was at about 66%. After 4 hours, the deesterification was almost 50%, and the oxazolidinone opening was at about 57%. Thus, deesterification slowed but the oxazolidinone appeared to be reformed as the TMSI was used up. The mixture was refluxed overnight, and after 22 hours the deesterification was up to 78% and the oxazolidinone mostly reformed. Another equivalent of TMSI was added, and after 1 hour deesterification was 84%, with much of the oxazolidinone opened. After an additional 2¾ hours, deesterification was 87%. One equivalent each of HMDS and TMSI was added, and in 1 hour deesterification was 90%, and in 2⅓ hours 92%. One more equivalent of each reagent was added, and after 1 hour the deesterification was at about 95% completion, and of this about 77% appeared to have the oxazolidinone ring opened. After cooling to 5° C., 1,4-Diazabicyclo(2.2.2)octane (DABCO) (0.504 g, 4.5 mM) was added, and the mixture was stirred overnight at room temperature. HPLC at about 15½ hours showed an excellent reaction to the enamine. Concentrated HCl (0.29 ml in 1.61 ml H₂O) was added, dissolving the DABCO-HI complex and crystallizing the product (9a). The pH (5.2) was lowered to 4.0 with 3 drops of conc. HCl. The mixture was stirred 10 min., and the precipitate was filtered and washed with 16 ml ACN/H₂O (2/1), then 5 ml EtOAc. The material was vacuum dried at 50° C. to 0.155 g of an off-white solid (9a). HPLC showed 98% product, a crude yield of 71%. NMR (DMSO d-6, TFA): δ 2.00 (m, 2), 2.68 (m, 2), 3.95 (m, 1), 4.84 (d, 1), 8.88 (bs, 5).

Although not intending to be bound thereby, it is expected that the TMSI reaction with the methyl ester (8a) proceeds in accordance with the following reaction scheme:

TMSI Reaction Scheme - Methyl Ester

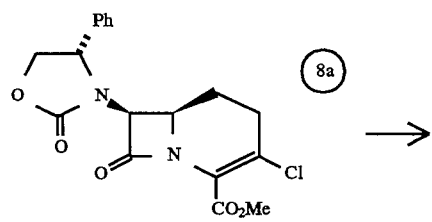

TMSI Reaction Scheme - Methyl Ester

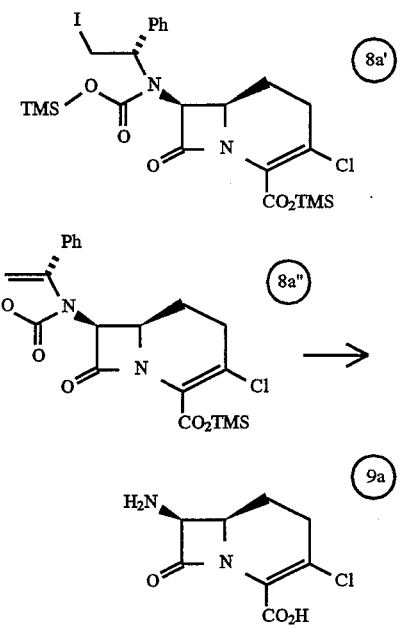

As shown, reaction of the methyl ester (8a) with the trimethylsilyl iodide (with HMDS and ACN) provides the oxazolidinone ring-opened product as the iodoethyl intermediate (8a'). Addition of the DABCO eliminates the iodide substituent to yield the enamine (8a"). Finally, hydrolysis upon addition of aqueous HCl leads to formation of the carbacephem, i.e. the (6R,7S)7-amino-3-chloro-1-azabicyclo[4,2,0]oct-2en-8-one-2-carboxylic acid (9a).

A weak non-nucleophilic base or HI scavenger is added with the TMSI to prevent extensive decomposition of the β-lactams. The preferred base is HMDS, i.e. 1,1,1,3,3,3-hexamethyldisilazane. It plays multiple roles in that it silylates the carboxylic acid when present, as well as scavenging any HI produced, while not deactivating the TMSI. Another non-nucleophilic base which may be employed with success is pyrimidine. Stonger bases such as triethylamine are not suitable since they complex with the TMSI too strongly and deactivate it. Alternatively, allyl trimethylsilane may be employed with success as an HI scavenger (a reaction which will produce TMSI) and as a silylating agent.

The preferred base for the elimination of HI from the iodoethyl intermediate is DABCO, i.e. 1,4-diazabicyclo[2.2.2]octane. Simple amine bases such as triethylamine are not effective. Other diazabicyclic bases also may be used with success, for example DBU (1,8-diazabicyclo[5.4.0]undec-7-ene) and DBN (1,5-diazabicyclo[4.3.0]non-5-ene). However, these are stronger than DABCO and cause more epimerization at C-7 in the β-lactam.

Preparation of Carbacephems Using Non-Methyl Carboxy Protecting Groups

By way of further example, an alternate synthesis route is demonstrated by a process in which a p-nitrobenzyl (PNB) ester is used as the carboxy protecting group. As will be seen subsequently, the use of a non-methyl ester modestly alters the synthesis technique, but maintains the advantage of retaining the amino protecting chiral auxiliary, until late in the procedure. This makes the process substantially more efficient, and results in high product yield. The process specifically described in the following Examples 8–15f proceeds as shown below:

Reaction Scheme III - PNB Carboxy Protecting Group

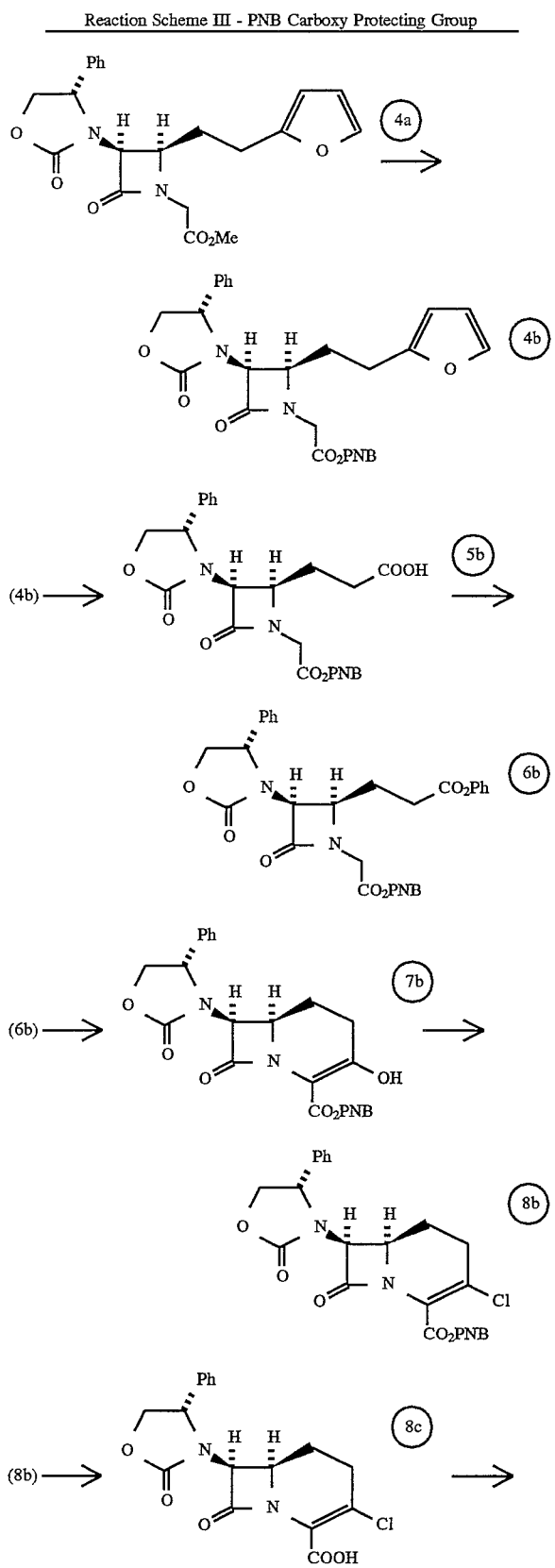

-continued
Reaction Scheme III - PNB Carboxy Protecting Group

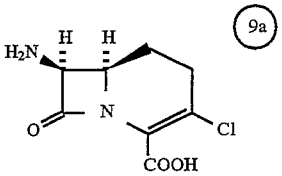

EXAMPLE 8

This process proceeded in the same manner as described in Examples 1 and 2, to yield the methyl ester (4a). The methyl ester was then converted to the PNB ester as follows. The methyl ester (4a) (180 g, 452 mM) was combined with 2500 ml tetrahydrofuran (THF) and cooled to 0° C. Then added to the mixture was 452 ml of water, followed by 452 ml 1N NaOH added dropwise over 10 min. HPLC about 2 min. after the base addition showed about 4% of a peak which could have been starting material and 75.7% for the product peak. After stirring 15 min., the pH was lowered to 8.5 with 15% $H_2SO_4$. The THF was evaporated on the rotary evaporator, and $H_2O$ was added back to give about a 1600 ml volume.

A 25 ml aliquot (from the 1600 ml) was removed and added thereto were 50 ml $CH_2Cl_2$, 100 ml EtOAc, 50 ml saturated bicarbonate and 100 ml $H_2O$. The bicarbonate extract was separated and washed with 25 ml EtOAc. 50 ml EtOAc was added, and the pH was adjusted to 2.0 with conc. HCl. The organic layer was separated and washed with brine and dried with $Na_2SO_4$ and evaporated to a 16.5 g slurry. This slurry was diluted with 15 ml ether, and the product acid (4c) was filtered and washed with ether to yield, upon vacuum drying, (A) 0.96 g. The filtrate gave 0.15 g (B) when evaporated to dryness.

To the remaining 1575 ml were added $CH_2Cl_2$ (2500 ml), p-nitrobenzyl bromide (102.5 g, 474.6 mM, a 5% excess), and tetrabutyl ammonium bromide (TBABr) (29.1 g). The pH was 9.5, and the temperature was about 23° C. After 1 hr. 40 min., HPLC showed the reaction was progressing normally. The mixture was stirred overnight at room temperature, and HPLC showed the reaction was finished. The aqueous layer was separated and washed with 100 ml $CH_2Cl_2$. The combined $CH_2Cl_2$ solution was washed with 1600 ml 10% brine and dried with $MgSO_4$. The resulting mixture was filtered on Hyflo and the $CH_2Cl_2$ was evaporated to a crystallizing syrup, which was slowly diluted with 2000 ml ether and 2000 ml isopropyl alcohol. The product was filtered and washed with ether/isopropyl alcohol (3/1), and vacuum dried at room temperature (the first 2 hours being at 50° C.) to (C) 212.8 g, a yield of 90.6% (without accounting for the aliquot taken to provide the acid product). The filtrate was allowed to evaporate in a large crystallizing dish to crystals in syrup, and this was slurried with 100 ml isopropyl alcohol and filtered with an isopropyl alcohol wash. The resulting material was vacuum dried at 50° C. to (D) 5.68 g, another 2.4% yield. Total yield was about 218.5 g. or 93%, showing excellent conversion to the PNB ester (4b). NMR of the product (C) was totally clean. HPLC of (C) was 98.9% and of (D) was 97.8%. HPLC of the acid (A) was 97.6%. NMR in deuterated dimethylsulfoxide (DMSO) was excellent (some $H_2O$ and ether were present). The m.p. of (A) was 191°–192° C.; the m.p. of (C) was 143.5°–144.5° C.; and the m.p. of (D) was 142°–143.5° C.

For the product acid (A), F.D. mass spec. showed "P" at 384. Titration gave pKa=5.8 in 66% DMF. Sp. rotation was +47.69 deg. at 589 nm and +138.28 deg. at 365 nm in $CHCl_3$ solvent. UV in EtOH showed no major absorption until a rise beginning at about 235 nm, peaking at about 200 nm. Analysis calculated: C, 62.49; H, 5.24; N, 7.29. Found: C, 62.62; H, 5.24; N, 7.18. NMR (DMSO d-6): δ 1.78 (m, 1), 1.95 (m, 1), 2.65 (m, 2), 3.68 (d, 1), 3.78 (q, 1), 4.03 (d, 1), 4.12 (dd, 1), 4.22 (d, 1), 4.69 (t, 1), 4.96 (dd, 1), 6.10 (d, 1), 6.34 (t, 1), 7.39 (m, 5), 7.51 (s, 1).

For the product ester (C), IR had β-lactam at 1759.5 $cm^{-1}$. UV showed a peak at 264 nm with ε=9990. Sp. rotation at 589 nm was +43.91 deg. in $CHCl_3$. F.D. mass spec. had P at 519. Analysis calculated for $C_{27}H_{25}N_3O_8$: C, 62.42; H, 4.85; N, 8.09. Found: C, 62.60; H, 4.91; N, 8.17. NMR (DMSO d-6): δ 1.81 (m, 1) 1.95 (m, 1), 2.63 (t, 1), 3.79 (q, 1), 3.95 (d, 1), 4.12 (dd, 1), 4.25 (d, 1), 4.26 (d, 1), 4.70 (t, 1), 4.97 (dd, 1), 5.23 (s, 2), 6.06 (d, 1), 6.32 (t, 1), 7.39 (,n, 5), 7.49 (s, 1), 7.60 (d, 2), 8.16 (d, 2).

EXAMPLE 9

Conversion of the furan PNB ester (4b) to the carboxylic acid (5b) was accomplished by ozonolysis as follows. The furan PNB ester (4b) (66.0 g, 127 mM) was combined at room temperature with 834 ml $CH_2Cl_2$ and 126 ml MeOH and cooled in dry ice/acetone. $N_2$ was purged in during the cool down period. The ozonator was set at 1.5 amps and a flow rate of $O_2$ adjusted to 5 SCFH (cylinder gauge at 2 psi). The ozonator was started and the $O_3$ stream was fed to the reaction solution. $CH_2Cl_2$ (166 ml) was added over 2 min. to thin the mixture. A definitive blue color was obtained at about 2 hr. The ozone inlet was replaced with a $N_2$ purge to remove the excess ozone (the blue color disappeared). The dry ice bath was removed and a room temperature water bath was applied. 30% $H_2O_2$ (43.2 ml, 380 mM) was rapidly added dropwise, and the resulting mixture was stirred to room temperature over about 2½ hrs. HPLC showed a slow conversion of intermediates to product acid (5b). The mixture was quenched with a solution of 55 g $NaHSO_3$ in 1000 ml $H_2O$ to a negative starch-iodide test, requiring most of this solution. HPLC showed 83% product. The $CH_2Cl_2$ layer was separated, washed with 3×500 ml of 5% NaCl and dried with $MgSO_4$. After refrigeration overnight, this mixture was filtered on Hyflo and evaporated to a slurry of gelatinous solid in $CH_2Cl_2$, about 1:1. The material was diluted slowly with 900 ml ether, stirred for 2 hr., and filtered. The white solid was washed with ether and vacuum dried to 61.5 g of product (5b). HPLC was 89.4%, giving a corrected yield of about 87%. NMR in $CDCl_3$ was excellent. M.P. was 78°–81° C. NMR ($CDCl_3$): δ 1.62 (m, 1), 1.86 (m, 1), 2.36 (t, 2), 3.76 (d, 1), 3.92 (q, 1), 4.34 (d, 1), 4.34 (dd, 1), 4.64 (d, 1), 4.77 (t, 1), 5.02 (dd, 1), 5.22 (s, 2), 7.43 (s, 5), 7.50 (d, 2), 8.22 (d, 2).

EXAMPLE 10

The carboxylic acid product (5b) (4.48 g, 9 mM) was added to 28 ml $CH_2Cl_2$ and cooled to –30° C. TEA (1.27 ml, 9.13 mM; 1.01 eq.) was then added, followed by the addition of 0.22 g (1.8 mM) DMAP. Phenyl chloroformate (1.52 ml, 12.1 mM, in 7 ml $CH_2Cl_2$) was added and the resulting mixture stirred for 20 minutes. HPLC showed the product diesher (6b) at 88%, with about 2% starting material. This did not change on warming to 0° C. Three drops of TEA were added with no effect. After quenching with 10.5 ml 1N HCl (10.5 mM) and stirring to room temperature, the product was separated, washed with brine, and dried with $MgSO_4$. Most of the $CH_2Cl_2$ was evaporated and then 23 ml EtOAc was added. The rest of the $CH_2Cl_2$ was evaporated, along with some of the EtOAc, until crystallization of the product began at about 15 ml volume. After adding about 8 ml ether, the crystals were sticky, so additional EtOAc (13 ml) was added to the ether. The mixture was eventually evaporated to a wet solid, slurried with 20 ml isopropyl acetate (iPrOAc), and 40 ml ether was slowly added. After filtering and washing with 20 ml of the same mix, the crystals were vacuum dried at 35° C. to 4.11 g of a white solid (A). Yield was 80%. The filtrate was evaporated to 1.3 g solid, slurried with 100 ml ether and set overnight at room temperature. This material was filtered and washed with 50 ml ether to give product (B) 0.68 g. Yield was 13%. HPLC of (A) was 94%, and of (B) was 85%. Total uncorrected isolated yield was about 93%. NMR in $CDCl_3$ was excellent (trace iPrOAc). F.D. mass spec. gave a parent at 573 but also something at 646 (possibly a recombination of fragments). Specific rotation ($CH_2Cl_2$, MeOH) was +46.66 deg. at 589 nm. UV peak at 264 nm had ε=10400. M.P. was 115°–118° C. IR in $CHCl_3$ had β-lactam at 1758 $cm^{-1}$. Analysis calculated for $C_{30}H_{27}N_3O_9$: C, 62.82; H, 4.75; N, 7.33. Found: C, 62.65; H, 4.70; N, 7.37. NMR ($CDCl_3$): δ 1.74 (m, 1), 1.93 (m, 1), 2.59 (t, 2), 3.77 (d, 1), 4.01 (q, 1), 4.34 (dd, 1), 4.37 (d, 1), 4.67 (d, 1), 4.76 (t, 1), 5.03 (dd, 1), 5.17 (s, 2), 7.06 (d, 2), 7.26 (t, 1), 7.38 (d, 2), 7.42 (s, 5), 7.44 (d, 2), 8.16 (d, 2).

EXAMPLE 11a

The product (6b) (4.00 g, 7 mM) was combined with 40 ml THF and cooled to –78° C., after which sodium t-pentoxide (2.31 g, 21 mM) was added and the mixture stirred. HPLC after 10 min. showed some phenyl ester remaining. The reaction finished slowly. After stirring at –78° for 70 min., the reaction mixture was poured into 100 ml $CH_2Cl_2$ and 100 ml 1N HCl stirring rapidly at room temperature. After 5 min. the organic layer was separated and washed with 2×100 ml $H_2O$, then with brine. The product solution was dried with $MgSO_4$ and $CH_2Cl_2$ evaporated on the rotary evaporator. The residue was crystallized with 30 ml EtOAc. After 10 min. this slurry was cooled in an ice bath. The product enol was filtered and washed with 20 ml cold EtOAc, then with ether. Vacuum drying at 35° C. gave A) 2.05 g, which was pure by HPLC. The filtrate was evaporated and the residue solid slurried with 5 ml EtOAc in an ice bath to obtain a second crop B) 0.24 g, which was also pure by HPLC. Total yield was 2.29 g for 68%. NMR ($CDCl_3$): δ 1.69 (m, 1), 1.91 (m, 1), 2.42 (m, 2), 3.70 (m, 1), 4.33 (dd, 1), 4.65 (d, 1), 4.77 (t, 1), 5.01 (dd, 1), 5.26 (d, 1), 5.49 (d, 1), 7.44 (m, 5), 7.70 (d, 2), 8.24 (d, 2), 11.18 (s, 1). Analysis calculated for $C_{24}H_{21}N_3O_8$: C, 60.13; H, 4.42; N, 8.78. Found: C, 60.40; H, 4.40; N, 8.62.

EXAMPLE 11b

Conversion of the carboxylic acid product (5b) to the enol (7b) (compare Examples 10 and 11a) was combined in the following procedure. 600 gms. (1.206M) of the carboxylic acid (5b) was added to 5400 ml of THF at r.t. 175.8 ml of TEA (1.26M) and 9.0 gm (73.8 mM) of DMAP were added. Added dropwise over 20 min. were 181.9 ml (1.45M) of phenyl chloroformate in 600 ml of THF at 30° C. After stirring for 10 min., the mixture was filtered to remove salts, followed by cooling of the phenyl ester solution to –15° C.

384 gm (4.8M) of lithium t-butoxide was dissolved in 6000 ml of THF, and the mixture was cooled to –15° C. The dissolved base was added to the phenyl ester dropwise over 5 to 10 min. (–10° C.), and the resulting mixture was stirred at –10° C. for 5 min. HPLC showed the reaction was complete. The reaction was quenched with 660 ml of conc. HCl in 3300 ml of 20% brine, and the mixture was stirred at 20° C. for 30 min. 3300 ml of water was added and the resulting material was separated into layers. The organic layer was stripped to a 6000 gm slurry. 6000 ml of isopropyl alcohol was added and the material was then stripped again to a 6000 gm slurry. Another 6000 ml of IPA was added and the resulting mixture was stripped to a 9000 gm slurry. This slurry was cooled to 0° C., stirred for 1–2 hrs., filtered and washed with IPA (2.75 L), and vac. dried at 35°–40° C. Weight of the enol product (7b) was 512.7 g. Yield was 88.7%. HPLC showed 98.8%. NMR (CDCl$_3$): δ 1.69 (m, 1), 1.90 (m, 1), 2.40 (m, 2), 3.67 (m, 1), 4.32 (dd, 1), 4.63 (a, 1), 4.75 (t, 1), 5.00 (ad, 1), 5.24 (d, 1), 5.47 (d, 1), 7.41 (m, 5), 7.68 (d, 2), 8.22 (d, 2), 11.17 (s, 1).

EXAMPLE 12a

A phosphite/Cl$_2$ adduct was prepared at −15° C. as described in Example 6. Triphenyl phosphite (2.13 ml, 8 mM) in 2 ml CH$_2$Cl$_2$, along with Cl$_2$ gas, were added to 30 ml CH$_2$Cl$_2$, and the slight excess of chlorine was quenched with a few drops of amylene. 1.0 g (ca. 8 mM) of polyvinyl pyridine polymer (PVPP), specially dried, first by toluene azeotrope and second by vacuum oven, was added, followed by addition of 1.92 g (4 mM) of the enol (7b). The cold bath was removed and a room temperature bath applied. The temperature went to room temperature in 3 min. The reaction mixture was stirred at room temperature (23°–24° C.) for 4 hours. This reaction was followed by HPLC and proceeded smoothly. After 4 hrs. at room temperature, the PVPP was filtered and the solution was washed with 50 ml H$_2$O and then with brine twice. The solution was dried with MgSO$_4$ and evaporated to a syrup which crystallized. The crystals were slurried with 25 ml ether for 20 min. and filtered with an ether wash. Vacuum drying of the white solid at 40° C. yielded 1.75 g of the chlorinated PNB ester (8b), a yield of 88%. NMR in CDCl$_3$ was excellent (showing a trace of ether). HPLC gave a purity of 94%. The major impurities were a fast moving peak corresponding to a deesterified product 8c (at 1.44 min.) and to the enol starting material (at 4.57 min.). I.R. gave β-lactam at 1783.9 cm$^{-1}$. UV gave a 271 nm peak with ε=18400. F.D. mass spec. gave parent ion at 497. M.P. 206°–207° C. Analysis calculated for C$_{24}$H$_{20}$Cl$_1$N$_3$O$_7$: C, 57.90; H, 4.05; N, 8.44; Cl, 7.12. Found: C, 57.64; H, 4.04; N, 8.25; Cl, 7.33. NMR (CDCl$_3$): δ 1.80 (m, 1), 1.94 (m, 1), 2.55 (m, 2), 3.76 (m, 1), 4.32 (dd, 1), 4.66 (d, 1), 4.76 (t, 1), 4.96 (dd, 1), 5.37 (q, 2), 7.43 (m, 5), 7.61 (d, 2), 8.22 (d, 2).

EXAMPLE 12b

A phosphite/Cl$_2$ adduct was prepared by simultaneous addition of Cl$_2$ gas and 73.2 ml (275 mM) triphenyl phosphite dropwise to 516 ml CH$_2$Cl$_2$, maintaining a temperature less than −15° C. with a dry ice, acetone bath. Excess Cl$_2$ was quenched with 2 ml of amylenes. Then 21.6 ml (275 mM) pyrimidine was added, followed by 66 g (137.5 mM) of enol (7b) and 516 ml EtOAc. The cold bath was removed and the reaction mixture warmed to room temperature and stirred 2.5 hours. HPLC showed the chlorination was complete. 1750 ml H$_2$O was added, and then 500 ml CH$_2$Cl$_2$, to aid the separation of layers. The organic layer was separated and washed with 2×1000 ml brine. It was dried with MgSO$_4$, filtered on Hyflo filter aid, and evaporated on the rotary evaporator to 290 g of slurry. 860 ml Et$_2$O was added slowly and the crystallization mixture stirred for 30 min. The product was filtered and washed with Et$_2$O and vacuum dried overnight to 59.9 g of the chlorinated PNB ester (8b), a yield of 87.5%. HPLC gave a purity of 96.3%. NMR (CDCl$_3$): δ 1.82 (m, 1), 1.93 (m, 1), 2.54 (m, 2), 3.74 (m, 1), 4.29 (dd, 1), 4.62 (d, 1), 4.74 (t, 1), 4.94 (dd, 1), 5.34 (q, 2), 7.40 (m, 5), 7.59 (d, 2), 8.20 (d, 2).

Cleavage of the Chiral Auxiliary and the Non-Methyl Carboxy Protecting Group The foregoing examples provided a 3-substituted compound including both the non-methyl, 2-carboxy protective group and the 7-amino protective chiral auxiliary. The following examples demonstrate alternative routes for conversion of such compounds to the corresponding carbacephems. In the procedures of Examples 13a–15f, the synthesis proceeds first with cleavage of the carboxy protecting group to yield the 2-carboxylic acid, which is then converted to the 7-amino carbacephem. In the alternative procedures of Examples 16–17, the cleavage of the chiral auxiliary proceeds prior to or simultaneously with the removal of the carboxy protecting group.

EXAMPLE 13a

The chlorinated PNB ester (8b) (4.98 g, 10 mM) was combined with 20 ml N,N-dimethylformamide (DMF) and 20 ml MeOH, and 2.16 g (33 mM) zinc dust was then added in portions. Methanesulfonic acid (CH$_3$SO$_3$H) (5.0 ml, 77 mM) was added dropwise over 30 min., giving an exotherm to 40° C. This temperature was held in a water bath. During the zinc acid reaction a precipitate formed, but this dissolved as the remainder of the acid was added. HPLC after 1 hr. 50 min. showed a clean reaction to the 2-carboxylic acid (8c). After 2 hr. at 40° C., the mixture was filtered and the zinc fines were washed with 10 ml DMF/H$_2$O (1/1). Added thereto were 100 ml CH$_2$Cl$_2$ and 100 ml H$_2$O, followed by stirring. The CH$_2$Cl$_2$ layer was separated and the aqueous layer was extracted again with 20 ml CH$_2$Cl$_2$, which removed all but a trace of product. The extracts were combined and washed with 100 ml 10% brine, dried with MgSO$_4$, and evaporated to 10.3 g syrup. The syrup was diluted with 25 ml isopropyl alcohol (iPrOH) and seeded. The product crystallized rapidly. iPrOH (35 ml) was added slowly and the mixture was stirred overnight at room temperature and then cooled to 0° C. for 1 hr., but the supernatant still contained some product. Hexane (25 ml) was added, and HPLC of the supernatant showed less product. After adding another 25 ml hexane and stirring at room temperature, HPLC of the supernatant showed little product. Filtering and washing with iPrOH/hexane (1/1), followed by vacuum drying at 50° C., yielded 2.63 g of a yellow solid (8c), a crude yield of 72%. NMR was fine (showing some DMF and some iPrOH). HPLC showed 99%. NMR (DMSO d-6): δ 1.98 (m, 2), 2.55 (m, 2), 3.78 (m, 1), 4.12 (dd, 1), 4.47 (d, 1), 4.73 (t, 1), 5.02 (dd, 1), 7.41 (m, 5), 13.5 (s, 1).

EXAMPLE 13b

The PNB ester cleavage of Example 13a was repeated with minor modifications. Primarily, HCl was used instead of the methanesulfonic acid. The chlorinated PNB ester (8b) (4.98 g, 10 mM) was combined with 50 ml DMF and cooled to 0°–5° C., and then added thereto was conc. HCl (8.75 ml, 105 mM). The starting material crystallized during the addition of the conc. HCl (at about 7 ml), so the mixture was warmed to room temperature and 5 ml DMF was added. With the start of the zinc addition (2.29 g, 35 mM), the mixture thinned and became stirrable. An ice bath was applied to hold room temperature (20°–25° C.), and a clear solution was soon obtained. The remainder of the conc. HCl and the zinc were added. The pH after 20 min. was 1.00, and after 1 hr. 35 min. was 1.13. The mixture was stirred 1 hr. 45 min., but even though there was no starting material the reduced ester was hydrolyzing slowly. The mixture was filtered with a 5 ml DMF wash on glass paper, and 30 ml H$_2$O was added to speed the hydrolysis, which it did dramatically. At 2 hr. 10 min. only 3% of the intermediate remained, and the pH was at 1.35. At 2 hr. 30 min., the reaction was essentially finished. H$_2$O (40 ml) was added dropwise and the hazy solution was seeded. Upon addition of an additional 70 ml H$_2$O dropwise, a gummy solid formed. CH$_2$Cl$_2$ (5 ml) was then added and the mixture was stirred for 30 min. The product crystallized, but was not of acceptable quality—also about 25% of the product was still in solution—so the mixture was extracted with 250 ml CH$_2$Cl$_2$ and then 100 ml CH$_2$Cl$_2$. The CH$_2$Cl$_2$ extracts were combined and washed with 100 ml 1N HCl. The organic layer was extracted with 2×100 ml saturated bicarbonate, and the bicarbonate extract was washed with 50 ml CH$_2$Cl$_2$. The bicarbonate extract was then filtered on Hyflo to remove some polymer. The pH of the bicarbonate extract was adjusted with conc. HCl to 1.5, with addition of some ether to control foaming due to CO$_2$ evolution. The product was filtered and washed with H$_2$O, then ether. The product (8c) was then vacuum dried at 50° C. to (A) 2.33 g, a yield of 64%. HPLC of the product was 99.5%. The filtrate sat for 8 days, and the ether was then evaporated. Another crop of product (pure by HPLC) was filtered and dried to (B) 0.42 g, a yield of 12%. Total yield: 76%.

EXAMPLE 13c

The chlorinated PNB ester (8b) (54.7 g, 109.9 mM) was added to 1165 ml of EtOAc. 21.97 g (164.8 mM) of lithium iodide was added, and the mixture was heated to reflux (78° C.) for 6.5 hours. The heat was shut off and the mixture was allowed to stir overnight to room temperature. 1098 ml of D.I. water and 220 ml of brine were added, and the mixture was stirred 5 min. The layers were separated. pH of the aqueous layer was lowered from 6.3 slowly with conc. HCl to 4.0 and seed crystals were added. Product crystallized at pH 3.5 to 4.2. The pH was then lowered to 1.9 and the mixture was stirred 15 minutes, and then filtered and washed with 750 ml H$_2$O. The product was vacuum dried at 60°–70° C. Weight of product was 34.48 g. Yield was 34.48/39.87= 86.5%. HPLC showed 98.3% product (8c).

EXAMPLE 13d

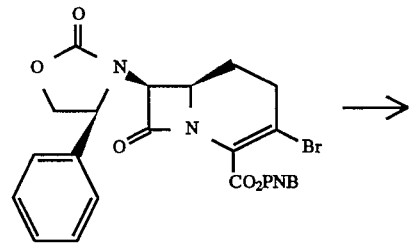

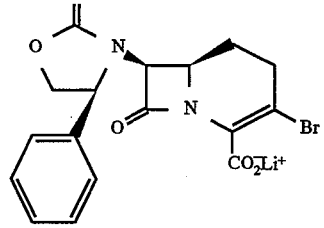

p-Nitrobenzyl 7β-[(S)-4-phenyloxazolidin-2-one-3-yl]-1-carba(1-dethia)-3-bromo-3-cephem-4-carboxylate (2.71 g, 5 mM) was slurried in tetrahydrofuran (30.5 ml), and lithium iodide (4.0 g, 30 mM) was added. The mixture was heated to reflux and stirred for about 4 hours. The formed precipitate was filtered and washed with 20 ml of tetrahydrofuran, then 15 ml of diethylether. The material was dried. The product lithium 7β-[(S)-4-phenyloxazolidin-2-one-3-yl]-1-carba(1-dethia)-3-bromo-3-cephem-4-carboxylate was obtained in a yield of 76.2%. Calculated analysis: C, 49.42; H, 3.42; N, 6.78; O, 19.36; Br, 19.34. Found: C, 49.39; H, 3.41; N, 6.53; O, 19.57; Br, 19.37. NMR (DMSO, TFA) δ 1.95 (m, 2); 2.68 (m, 2); 3.75 (m, 1); 4.10 (dd, 1), 4.45 (d, 1); 4.70 (t, 1); 4.98 (dd, 1); 7.35 (m, 5).

EXAMPLE 13e

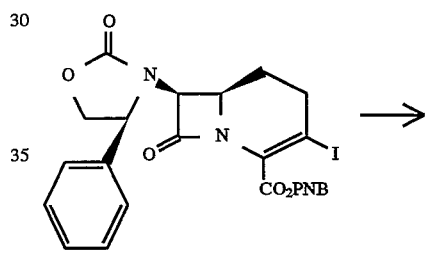

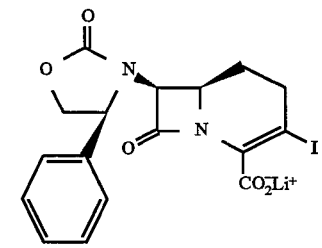

p-Nitrobenzyl 7β-[(S)-4-phenyloxazolidin-2-one-3-yl]-1-carba(1-dethia)-3-iodo-3-cephem-4-carboxylate (2.95 g, 5 mM) was dissolved in tetrahydrofuran (30.5 ml), and lithium iodide (4.0 g, 30 mM) was added. The mixture was heated to reflux and stirred for about 7.5 hours to form a solid. After removing the heat, 30 ml of ethyl acetate was added to the mixture. The mixture was allowed to cool to room temperature, and the formed solid was filtered and washed with 30 ml of a 50/50 mixture of tetrahydrofuran/ethyl acetate, then 15 ml of ethyl acetate, and then 10 ml of diethyl ether. The solid was dried. The product Lithium 7β-[(S)-4-phenyloxazolidin-2-one-3-yl]-1-carba(1-dethia)-3-iodo-3-cephem-4-carboxylate was obtained in an uncorrected yield of 65.6%. Calculated analysis: C, 44.37; H, 3.07; N, 6.09; I, 27.58. Found: C, 44.10; H, 3.04; N, 5.80; I, 27.38. NMR (DMSO, TFA) δ 1.88 (m, 2); 2.68 (m, 2); 3.75 (m, 1); 4.08 (dd, 1), 4.43 (d, 1); 4.68 (t, 1); 4.98 (dd, 1); 7.35 (m, 5).

EXAMPLE 13f

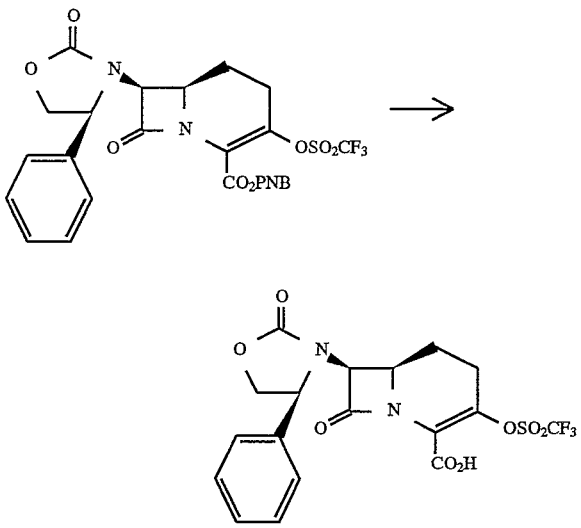

Lithium iodide (2.0 g, 15 mM) was added to p-nitrobenzyl 7β-[(S)-4-phenyloxazolidin-2-one-3-yl]-1-carba(1-dethia)-3-trifluoromethylsulfonyloxy-3-cephem-4-carboxylate (3.06 g, 5 mM) in 30 ml of ethyl acetate. The mixture was stirred for about 48 hours at room temperature and the reaction was finished by HPLC. Thereafter, 50 ml of water was added to the solution. The aqueous and organic layers were separated. The aqueous layer was placed in a rotary evaporator and a small amount of ethyl acetate was evaporated. A small amount of solids was then filtered off. The pH of the aqueous layer was then lowered from 7.34 to about 1.89 using concentrated HCl. At a pH of about 3.5, solid began to precipitate. The mixture was shirred at the pH of 1.89 for about 10 minutes, then the solid was filtered and washed with 10 ml of water and 15 ml of diethyl ether. The solid was dried. The product 7β-[(S)-4-phenyloxazolidin-2-one-3-yl]-1-carba(1-dethia)-3-trifluoromethylsulfonyloxy-3-cephem-4-carboxylic acid was obtained in a yield of 50%. Calculated analysis: C, 45.38; H, 3.17; N, 5.88. Found: C, 45.65; H, 3.31, N, 6.05. NMR (DMSO) δ 1.95 (m, 1); 2.03 (m, 1); 2.55 (m, 2); 3.78 (m, 1); 4.03 (dd, 1); 4.52 (d, 1); 4.70 (t, 1); 5.02 (dd, 1); 7.40 (m, 5).

EXAMPLE 13g

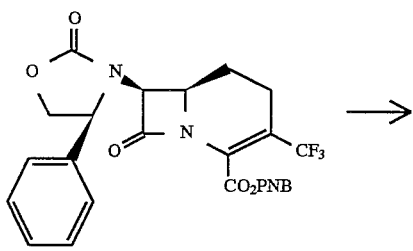

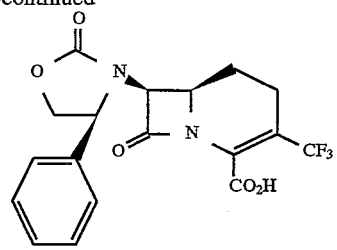

Lithium iodide (1.67 g, 12.5 mM) was added to p-nitrobenzyl 7β-[(S)-4-phenyloxazolidin-2-one-3-yl]-1-carba(1-dethia)-3-trifluoromethyl- 3-cephem-4-carboxylic acid (5.31 g, 10 mM) in 106 ml of ethyl acetate. The mixture was heated to reflux and stirred for about 6.5 hours. Thereafter, the mixture was stirred at room temperature for 3 days. Water (100 ml) was added, followed by saturated brine (20 ml). The layers were separated. The pH of the aqueous layer was lowered slowly to 4.0 by addition of concentrated HCl and the mixture was seeded. The pH was further lowered to 1.9 and the mixture was stirred for 15 minutes. The formed solid was filtered and washed with 50 ml of water and vacuum dried at 60° C., yielding 3.20 g of the product 7β-[(S)-4-phenyloxazolidin-2-one-3-yl]-1-carba (1-dethia)-3-trifluoromethyl-3-cephem-4-carboxylic acid, an uncorrected yield of 81%. Analysis calculated for $C_{18}H_{15}N_2O_5F_3$: C, 54.55; H, 3.82; N, 7.07; F, 14.38. Found: C, 54.78; H, 3.97; N, 6.87; F, 14.45. NMR (DMSO d-6): δ 1.67 (m, 1), 2.07 (m, 1), 2.29 (m, 2), 3.79 (m, 1), 4.12 (dd, 1), 4.58 (d, 1), 4.73 (t, 1), 5.02 (dd, 1), 7.39 (m, 5), 14.04 (bs, 1).

EXAMPLE 14a

The 2-carboxylic acid (8c), as produced in Example 13a, was converted to the carbacephem (9a) through reaction with trimethylsilyl iodide (TMSI). Specifically, the carboxylic acid (8c) (0.726 g, 2 mM), was combined with 5 ml acetonitrile (ACN), HMDS (1.06 ml, 5 mM), and TMSI (0.72 ml, 5 mM), and the mixture was stirred for 4 hours at room temperature. DABCO (0.56 g, 5 mM) in 5 ml ACN was added and the solution stirred overnight at room temperature, yielding a DABCO-HI precipitate. Both reactions appeared normal and the DABCO reaction (elimination) gave an HPLC ratio of product to starting material of 39.1/12.0 for a conversion of about 77%. 5 ml of 1N HCl was added and the mixture stirred for 30 min. at room temperature. The pH was at 3.55. The DABCO-HI precipitate dissolved and the desired carbacephem product (9a) appeared as a precipitate. The product was filtered and washed successively with 10 ml of ACN/H₂O (2/1), 5 ml of H₂O, and 5 ml of ACN. Vacuum drying at 50° C. yielded 0.275 g of a nearly white solid. Yield was about 63.5%. NMR was excellent in DMSO (d-6) with trifluoroacetic acid (TFA) to dissolve. NMR (DMSO d-6, TFA): δ 1.95 (m, 2), 2.67 (m, 2), 3.94 (m, 1), 4.83 (d, 1), 8.57 (bs, 5).

As described with respect to Example 7, it is expected that the TMSI reaction produces the oxazolidinone ring-opened, iodoethyl intermediate. Addition of the HI elimination reagent and scavenger DABCO yields the enamine, and hydrolysis takes this product to the desired carbacephem (9a).

EXAMPLE 14b

The TMSI reaction of Example 14a was substantially duplicated, but was run in CH₂Cl₂ rather than acetonitrile.

The 2-carboxylic acid (8c) (0.363 g, 1 mM) was combined with 10 ml $CH_2Cl_2$. HMDS (0.43 ml, 2 mM) and TMSI (0.36 ml, 2.5 mM) were added thereto. The mixture was stirred for 1 hour, and then additional HMDS (0.1 ml, 0.5 mM) was added. The resulting solution was stirred overnight at room temperature and then additional HMDS (0.11 ml, 0.5 mM) and TMSI (0.07 ml, 1.5 mM) were added before mixing for 1 hour. The TMSI reaction gave a small HPLC peak at 4.8 min., probably because of the TMSI being present in excess over the HMDS. Otherwise it was clean to 13% starting material and 73% iodoethyl intermediate. DABCO (0.34 g, 3 mM) was added at 0° C. The ice bath was removed and the temperature rose to room temperature. The DABCO addition gave an immediate precipitate and slowly resulted in elimination to the enamine. After 4 hr. 40 min., another 1 eq. of DABCO was added and the solution stirred overnight. The reaction appeared to have stopped at about 18/49 product/starting material. Another 0.5 ml TMSI (about 3½ mM) was added, and yielded significant conversion of the starting material to the iodoethyl intermediate. Another 0.29 ml TMSI (about 2 mM) was added and the mixture was stirred overnight. HPLC showed much iodoethyl intermediate at 3.59 min. and the enamine product was not affected. The amount of starting material was at only 6%. Addition of 0.62 g (5.5 mM) DABCO gave 8.5 eq. TMSI and 9.5 eq. DABCO in this reaction. Elimination began again, and after 3 days at room temperature, HPLC showed a ratio of product to starting material of about 30% to 10% or about 3/1. The reaction mixture was light in color. The addition of 5 ml $H_2O$ gave complete solution of the precipitate in 3 min. The pH was at 4.8, and was lowered with conc. HCl to 2.0 for 5 min. The pH was then raised to 3.9 with TEA, showing no precipitate. Addition of 5 ml ACN raised the pH to 4.0, and another 5 ml ACN resulted in some precipitation. The product was filtered from the two phase mixture, and was washed with a mixture of 4 ml $H_2O$ and 10 ml ACN, and then with ether. The product was vacuum dried at 40° C. for 2 hr. to yield 0.115 g of a near white solid. HPLC was 98.6% for a yield of about 53% of the carbacephem (9a). Analysis calculated for $C_8H_9Cl_1N_2O_3$: C, 44.36; H, 4.19; N, 12.93; C, 16.37. Found: C, 42.62; H, 4.15; N, 11.95; Cl, 16.08. NMR (DMSO d-6, TFA): δ 1.97 (m, 2), 2.69 (m, 2), 3.94 (m, 1), 4.86 (d, 1), 8.91 (bs, 5).

EXAMPLE 14c

The 2-carboxylic acid (8c) (30.0 g, 82.7 mM) was added to 415 ml of acetonitrile at room temperature. 43.72 ml (207 mM, 2.5 eq.) of HMDS was added, followed by 29.81 ml (207 mM, 2.5 eq.) of TMSI. The mixture was allowed to stir for 6 hours at room temperature. HPLC showed the reaction was complete. The reaction was cooled to 0°–5° C., and 27.8 g (248.1 mM, 3.0 eq.) of DABCO was added (slight exotherm). The mixture was stirred at 0°–10° C. overnight. HPLC showed the reaction was complete.

When the reaction was completed, 248 ml of 1N HCl was added (temperature rose from 8° C. to 24° C. during hydrolysis). Product precipitated quickly. pH=4.1. The pH was lowered to 3.7 with conc. HCl as necessary (amt. of HCl used was 4.0 ml), and the mixture was stirred for 30 minutes at room temperature. The mixture was then filtered and washed with ACN:$H_2O$ (2:1, 250 ml), washed with 350 ml of ACN, and vacuum dried at 60° C. Weight of product was 12.44 g. Yield was 69.6%. HPLC showed 91.8% product (9a).

EXAMPLE 15a

In another alternate procedure, the carboxylic acid (8c) (0.363 g, 1 mM) was combined with 3.8 ml ACN at 0° C., and 0.32 ml (2 mM) of allyl trimethylsilane was added thereto. One drop of TMSI was added, and after 70 min. a second drop of TMSI was added, both followed with stirring. The allyl trimethylsilane silylated the acid group of the starting material (8c) under catalytic HI from the TMSI reaction. The suspension cleared or thinned considerably after the first drop of TMSI and cleared completely after the second drop and another 1 hour of stirring at room temperature. HPLC showed no degradation. A full equivalent of TMSI (0.14 ml, 1 mM) was added and, after 1 hour, HPLC showed a clean reaction to the ring-opened intermediate iodide. The allyl trimethylsilane was a good HI scavenger. The mixture was stirred overnight at room temperature, but the oxazolidinone opening had progressed very little past the result of the first hour. Another equivalent of TMSI was added. In 2 hours, HPLC showed a ratio of starting material to intermediate of 13.6/66.3 for an 83% reaction. In 3 hours, the conversion was at 86%. At this point, 2 eg. of DABCO (0.22 g, 2 mM) were added, followed by stirring for 4 days. HPLC showed much reversion to the starting material oxazolidinone. The ratio of product to starting material was 34/23.4 or 59% reaction. $H_2O$ (1.6 ml) was added, followed by stirring for 30 min. at pH 4.0. The mixture was filtered and washed with 6 ml ACN/$H_2O$ (2/1). Drying yielded 0.095 g of product (9a), a 44% yield.

EXAMPLE 15b

The foregoing TMSI, HMDS procedure was repeated, except with the 3-trifluoromethyl substituted 2-carboxylic acid. A 100 ml jacketed flask was charged with 15 ml ACN, and added thereto was HMDS (2.64 ml, 12.5 mM) and TMSI (1.80 ml, 12.5 mM). The solution turned light yellow. The 3-trifluoromethyl, 2-carboxylic acid (1.98 g, 5 mM) was then added and the flask was rinsed with the remaining 10 ml of ACN. The solid went into solution in about 1–2 min., and the solution was then stirred at room temperature for 6 hours. The coolant (–3° C.) was turned on to cool the flask to 0° C., and after about 20 min., the DABCO (1.68 g, 15 mM) was added. A precipitate immediately formed. The mixture was stirred cold overnight.

HPLC showed product was present. With the coolant off, 15 ml 1N HCl was added to the solution, and the temperature then rose to 17° C. The pH was adjusted with conc. HCl from 4.34 to 3.66. The mixture was stirred for 30 min., and the precipitate which slowly formed was filtered out. The precipitate was washed with 15 ml ACN/$H_2O$ (2/1), then 20 ml ACN, to give a white, powdered product (3-trifluoromethyl carbacephem), which was dried in a vacuum oven to 0.77 g, a 61.6% yield. NMR indicated product with a small amount of $H_2O$ and starting material in the sample. NMR (DMSO d-6, TFA): δ 1.76 (m, 1), 2.03 (m, 1), 2.37 (m, 2), 3.94 (m, 1), 4.84 (d, 1), 8.83 (bs, 5).

EXAMPLE 15c

The procedure of Example 15b was repeated using the 3-iodo carboxylic acid. HMDS (1.06 ml, 5 mM) and TMSI (0.71 ml, 5 mM) were added to a solution of the 3-iodo compound (0.91 g, 2 mM) in 10 ml ACN which had been azeotropically dried by distillation of 20 ml ACN. At 4 hr., the reaction seemed to be progressing well, yielding a precipitate. At 5½ hours, the intermediate peak was 75%. The solution was cooled down to 5° C. and the DABCO (0.67 g, 6 mM) was added. The precipitate changed slightly in consistency and color. The mixture was stirred at 3° C. overnight.

HPLC showed 22% product and 33% starting material. The intermediate reconverted to starting material, possibly due to H₂O getting into the reaction. After removing the cold bath, 6 ml of 1N HCl was added, and a precipitate formed. ACN (5 ml) was added to this, which dissolved some of the precipitate (starting material). The mixture was then filtered and washed with 5 ml ACN. The solid product still contained some starting material, and was therefore slurried in 5 ml ACN. The filtrate contained no product. The product was refiltered and washed with 5 ml ACN, and still had 3.7% starting material in it. Drying in an oven yielded 0.20 g of the 3-iodo carbacephem, a 32.7% yield. NMR showed product with some starting material and NH₄I present. NMR (DMSO d-6, TFA): δ 1.85 (bs, 2), 2.77 (m, 2), 3.93 (m, 1), 4.80 (d, 1), 8.89 (bs, 5).

EXAMPLE 15d

The procedure of Example 15b was repeated for the 3-bromo carboxylic acid (0.813 g, 2 mM), using 10 ml ACN, 1.06 ml (5 mM) HMDS and 0.71 ml (5 mM) TMSI. The reaction mixture was stirred at room temperature overnight, cooled to 0° C., and DABCO (0.67 g, 6 mM) was added, forming a light yellow precipitate. This mixture was stirred overnight at 0° C. and the coolant then turned off. To the mixture was then added 1N HCl (6 ml), and the pH was adjusted with additional conc. HCl from 4.51 to 3.71. The product appeared as a precipitate. The mixture was stirred for ½ hr., then filtered and washed with 10 ml ACN/H₂O (2/1), and then 10 ml ACN. The product, which was white and clumped together some, was dried in a vacuum oven at 50° C. to 0.18 g, an uncorrected yield of 34.4%. HPLC showed that the product had about 3% starting material left in it. NMR looked good for product, showing some starting material and ammonium salt present. NMR (DMSO d-6, TFA): δ 1.94 (m, 2), 2.74 (m, 2), 3.93 (m, 1), 4.81 (d, 1), 8.88 (bs, 5).

EXAMPLE 15e

The TMSI reaction was repeated for the 3-triflate (OSO₂CF₃) carboxylic acid. The triflate starting material (0.95 g, 2 mM) was dissolved in 30 ml ACN, and 20 ml of the ACN was then distilled off to dry the starting material. The solution was cooled to room temperature, and then HMDS (1.06 ml, 5 mM) and TMSI (0.71 ml, 5 mM) were added. No precipitate appeared at first, but over a few hours a precipitate began to come out. At 6 hours, a small amount of the intermediate was present. The solution was then cooled to 0°–3° C. in an ice bath, and the DABCO (0.56 g, 5 mM) was added, yielding a precipitate. The mixture was stirred overnight, allowing the temperature to rise to room temperature. 1N HCl (6 ml) was added to the solution and all of the precipitate dissolved. The pH was adjusted using bicarbonate solution (10%) from 2.38 to 3.7. A solid slowly came out of solution. The mixture was stirred for ½ hour, then filtered and washed with 9 ml H₂O/ACN (½), then 5 ml ACN, to get a white solid. HPLC showed it was 96% pure 3-triflate carbacephem nucleus, which was dried in an oven to 0.14 g, 21% yield. The filtrate contained only about 3% product. NMR (DMSO d-6, TFA): δ 1.97 (m, 1), 2.07 (m, 1), 2.64 (m, 2), 3.97 (m, 1), 4.86 (d, 1), 8.82 (bs, 5).

EXAMPLE 15f

The TMSI reaction was scaled up for the 3-trifluoromethyl substituted 2-carboxylic acid. 470 g (1.187M) of the 3-trifluoromethyl compound was added to 5.94 L ACN at room temperature and treated with 627 ml (2.967M) of HMDS, followed by 427 ml (2.967M) of TMSI. After stirring for 6 hours at room temperature, HPLC indicated the reaction was finished. It was cooled to 0°–5° C. and 399 g (3.56M) of DABCO added. This mixture was stirred at 0°–10° C. overnight. HPLC indicated the elimination reaction was finished. 3.56 L of 1N HCl was added, giving an exotherm to 26° C. The hydrolysis product precipitated quickly. The pH of 4.25 was lowered with conc. HCl (60 ml) to 3.7. After stirring for 30 min. at room temperature, the product was filtered and washed with 2:1 ACN, H₂O (3.56 L) followed by ACN (4.75 L). Vacuum drying at 60° C. overnight gave 250.7 g of the 3-trifluoromethyl carbacephem, a yield of 84.4%. HPLC showed 92.5%, with 5.5% of a known impurity which carried through from the starting material. NMR (DMSO d-6, TFA): δ 1.75 (m, 1), 2.03 (m, 1), 2.38 (m, 2), 3.97 (m, 1), 4.88 (d, 1), 8.85 (bs, 5).

EXAMPLE 16

As an alternative to the foregoing PNB-TMSI procedures of Examples 13a–15e, the chiral auxiliary side chain can be removed prior to or simultaneously with the cleavage of a non-methyl, carboxy protecting group, as demonstrated hereafter. This synthesis route is exemplified by the following reaction scheme:

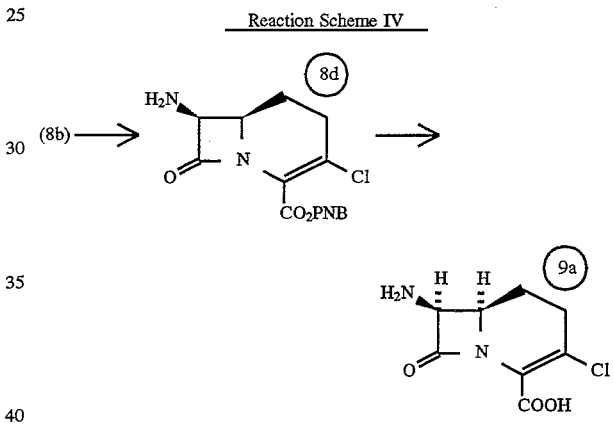

The chlorinated PNB ester (8b) (0.50 g, 1 mM) was combined with 10 ml CH₂Cl₂ at room temperature. TMSI (0.29 ml 2 mM) and HMDS (0.43 ml, 2 mM) were added, and the mixture stirred at room temperature for 1 hour. About 19% of the starting material was converted to the ring-opened intermediate iodide after 40 min. The mixture was then heated to reflux and proceeded to about 34% intermediate in 10 min., 40% in 30 min., 43% in 45 min., and 45% in 1 hr. 45 min. After refluxing for 6 hours, the iodoethyl intermediate was at 46.6%. The reaction mixture set for 16 hours at room temperature, after which some NH₄⁺I⁻ was coated on the condenser. Addition of another eq. HMDS (0.21 ml, 1 mM) gave reversal to starting material, leaving only 18% intermediate. Addition of another eq. TMSI (0.14 ml, 1 mM) changed the hydrolysis conditions and 46% intermediate appeared right away on HPLC. This grew to 61% in about 55 min. Adding ½ eq. each HMDS and TMSI gave 28% starting material and 46% intermediate, which resulted from the hydrolysis conditions becoming basic. The proportion of intermediate increased with quenching into ½ ml MeOH with 1 drop H₃PO₄. Additional TMSI (0.5 eq.) seemed to push the reaction at first, but it then stalled at 10% starting material. Another ¼ eq. TMSI decreased the starting material to 7.7% in 5 min. and not much further in 35 min. The reaction mixture was cooled to −10° C., and 1,8-Diazabicyclo[5.4.0]-undec-7-ene (DBU)

(4.25 mM) was added dropwise via a syringe. The resulting exotherm raised the temperature to 0° C., and HPLC showed reversion to starting material, simply meaning that elimination had not yet occurred and hydrolysis conditions were basic. After 30 min. at 0° C. much elimination had occurred, giving the desired 7-amino product (8d) at 2.10 min. and acetophenone at 1.58 min. via hydrolysis of the resulting enamine and silyl carbamate.

After 1 hr. 25 min., the reaction was about ⅔ done. After several hours at 0° C., the mixture was placed in the freezer at −16° C. overnight. HPLC showed a good reaction with only 8% starting material. The peak at 1.13 min. grew slowly, indicating the presence of the carbacephem nucleus resulting from de-esterification. HCl (conc., 0.33 ml) was added directly to the $CH_2Cl_2$ reaction solution with stirring at 0° C. The ice bath was removed and the temperature was allowed to rise to room temperature. The resulting precipitate was filtered and washed with $CH_2Cl_2$, and then dried to (A) 0.24 g of a beige solid. HPLC indicated product (8d) hydrochloride (almost no iodide by HPLC), and also much carbacephem nucleus (9a) from the ester cleavage. EtOAc (20 ml) was added to the filtrate, and precipitated an oily solid. The solvent (containing mostly acetophenone) was decanted and the solids (B) were dissolved in $CH_2Cl_2$, and 0.1 ml conc. HCl was added thereto. Some precipitate was obtained, but the mixture was gummy. The mixture was evaporated and the resulting material was stirred in 25 ml $CH_2Cl_2$. Filtering yielded an orange/red solid (C). NMR in DMSO was ok for product (C) and showed the carbacephem (9a), and also a large $—NH_3^+$ signal.

EXAMPLE 17

The trimethylsilyl iodide reaction of Example 16 removed the chiral auxiliary side chain to the amine, and also cleaved some of the PNB ester, giving a product which was part carbacephem nucleus (9a) and part nucleus ester (8d). This product mix was carried on through the following ester cleavage reaction.

The product of Example 16 (0.22 g) was combined with 5 ml DMF and 1 ml $H_2O$, and placed in an ice bath. Conc. HCl (0.5 ml) and zinc dust (0.13 g, 2 mM) were added and the ice bath removed. The temperature rose to 15° C. in 30 min., at which time ester removal appeared to be complete by HPLC. The mixture was filtered on glass paper to remove the zinc fines, which were washed with 1 ml DMF. The pH of the solution was adjusted with TEA from 1.2 to 4.5. The solution remained clear for less than a minute, then product began to crystallize. The mixture was cooled in an ice bath and then filtered with a 1 ml DMF wash, then acetonitrile. The product was a light cream color, and was vacuum dried to 0.027 g (9a). HPLC was excellent at 99%. HPLC of the filtrate showed a small amount of product. Overall yield from the initial PNB ester (8b) of Example 16 was about 12½%. 5 mg of the product was dissolved in DMSO by addition of 1 drop trifluoroacetic acid, and an NMR was run which was consistent with the desired carbacephem product (9a). NMR showed traces of DMF, $NH_4Cl$, TEA, and possibly the C-7 epimer (estimated about 5%). UV peak at 264 nm had ε=2740. M.P. 203° C. with decomposition. Theoretical analysis: C, 44.35; H, 4.19; N, 12.93; Cl 16.37. Calculated analysis: C, 43.70; H, 4.55; N, 13.16; Cl 15.89. NMR (DMSO d-6, TFA): δ 1.91 (m, 1), 2.00 (m, 1), 2.69 (m, 2), 3.94 (m, 1), 4.84 (d, 1), 8.92 (bs, 5).

While the invention has been described in detail in the foregoing description, the same is to be considered as illustrative and not restrictive in character, it being understood that only the preferred embodiments have been described and that all changes and modifications that come within the spirit of the invention are desired to be protected.

What is claimed is:

1. A compound of the formula:

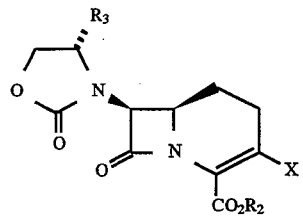

in which:

$R_2$ is a carboxy protecting group or hydrogen;

$R_3$ is selected from the group consisting of phenyl, $C_1$–$C_4$ alkylphenyl, halophenyl, $C_1$–$C_4$ alkoxyphenyl, naphthyl, thienyl, furyl, benzothienyl and benzofuryl; and X is selected from the group consisting of hydroxyl, halo, $C_1$–$C_6$ alkyl, $C_1$–$C_6$ alkyl substituted with cyano, carboxy, halogen, amino, $C_1$–$C_4$ alkoxy, $C_1$–$C_4$-alkylthio, trifluoromethyl or trifluoromethylthio, $C_1$–$C_4$ alkoxy, $C_1$–$C_4$ alkylthio, trifluoromethyl, $C_2$–$C_6$ alkenyl, $C_2$–$C_6$ alkenyl substituted by one or more halogen, hydroxy, protected hydroxy, nitro or trihalomethyl groups, $C_2$–$C_6$ alkynyl, $C_2$–$C_6$ alkynyl substituted by one or more of halogen, hydroxy, protected hydroxy, nitro or trihalomethyl, phenyl, phenyl substituted with a and/or a', wherein a and a' independently are hydrogen, halogen, hydroxy, $C_1$–$C_4$ alkoxy, $C_1$–$C_4$ alkanoyloxy, $C_1$–$C_4$ alkyl, $C_1$–$C_4$ alkylthio, amino, mono- or di($C_1$–$C_4$ alkyl)amino, $C_1$–$C_4$ alkanoylamino, $C_1$–$C_4$ alkylsulfonylamino, carboxy, carbamoyl, hydroxymethyl, aminomethyl, or carboxymethyl, $C_1$–$C_6$ alkyloxymethyl, phenyl-$C_1$–$C_6$ alkyloxymethyl, tri($C_1$–$C_6$)alkylsilyloxymethyl, trifluoromethylsulfonyloxy, cyano and phenoxy.

2. The compound of claim 1 in which $R_2$ is selected from the group consisting of methyl and p-nitrobenzyl.

3. The compound of claim 2 in which X is hydroxyl.

4. The compound of claim 3 and which is [7(4S),7S,6R]-7-[4-phenyl-2-oxazolidinone-3-yl]-3-hydroxy-8-oxo-1-azabicyclo[4.2.0]oct-2-ene-2-carboxylic acid methyl ester.

5. The compound of claim 3 and which is [7(4S),7S,6R]-7-[4-phenyl-2-oxazolidinone-3-yl]-3-hydroxy-8-oxo-1-azabicyclo[4.2.0]oct-2-ene-2-carboxylic acid (4-nitrophenyl)methyl ester.

6. The compound of claim 2 in which X is chloro.

7. The compound of claim 6 and which is [7(4S),7S,6R]-7-[4-phenyl-2-oxazolidinone-3-yl]-3-chloro-8-oxo-1-azabicyclo[4.2.0]oct-2-ene-2-carboxylic acid methyl ester.

8. The compound of claim 6 and which is [7(4S),7S,6R]-7-[4-phenyl-2-oxazolidinone-3-yl]-3-chloro-8-oxo-1-azabicyclo[4.2.0]oct-2-ene-2-carboxylic acid (4-nitrophenyl)methyl ester.

9. The compound of claim 1 in which $R_2$ is hydrogen and in which X is chloro.

10. The compound of claim 9 and which is [7(4S),7S,6R]-7-[4-phenyl-2-oxazolidinone-3-yl]-3-chloro-8-oxo-1-azabicyclo[4.2.0]oct-2-ene-2-carboxylic acid.

\* \* \* \* \*